United States Patent [19]
Burcoglu

[11] Patent Number: 5,977,083
[45] Date of Patent: Nov. 2, 1999

[54] METHOD FOR USING POLYNUCLEOTIDES, OLIGONUCLEOTIDES AND DERIVATIVES THEREOF TO TREAT VARIOUS DISEASE STATES

[76] Inventor: Arsinur Burcoglu, 213 Sweetgum Rd., Pittsburgh, Pa. 15238

[*] Notice: This patent is subject to a terminal disclaimer.

[21] Appl. No.: 08/465,352

[22] Filed: Jun. 5, 1995

Related U.S. Application Data

[63] Continuation-in-part of application No. 08/002,395, Jan. 13, 1993, abandoned, which is a continuation-in-part of application No. 07/748,277, Aug. 21, 1991, abandoned, application No. 07/815,130, Dec. 27, 1991, abandoned, and application No. 07/830,886, Feb. 4, 1992, abandoned.

[51] Int. Cl.$^6$ ............................ A61K 48/00; C12Q 1/68; C07H 21/04
[52] U.S. Cl. .................................... 514/44; 435/5; 435/6; 536/23.1; 536/24.3; 536/24.31; 536/24.32; 536/24.33; 536/24.5
[58] Field of Search ............................ 435/6, 5; 514/44; 536/24.5, 24.3–24.33, 23.1

[56] References Cited

U.S. PATENT DOCUMENTS

| | | |
|---|---|---|
| 3,770,720 | 11/1973 | Butti . |
| 3,829,567 | 8/1974 | Butti . |
| 3,899,481 | 8/1975 | Butti . |
| 4,374,856 | 2/1983 | Ruwart ................................... 424/317 |
| 4,649,134 | 3/1987 | Bonomi . |
| 4,693,995 | 9/1987 | Prino . |
| 4,795,744 | 1/1989 | Carter ....................................... 514/44 |
| 4,938,873 | 7/1990 | Rossi . |

FOREIGN PATENT DOCUMENTS

| | | |
|---|---|---|
| 1187830 | 4/1970 | European Pat. Off. . |
| 0 025 766 | 3/1981 | European Pat. Off. . |
| 0 152 148 | 2/1985 | European Pat. Off. . |
| 264 926 A1 | 2/1989 | Germany . |
| WO 94/15621 | 7/1994 | WIPO . |

OTHER PUBLICATIONS

Golboa et al. TIG 10: 139–144, 1994.

Orkin et al. Report and Reccomendations of the Panel to Assess the NIH Investment in Research on Gene Therapy, 1995.

Cook et al., "Effect of Reovirus Infection and Dietary Levels of Selected Vitamins on Immuoncompetence of Chickens," Chemical Abstract No. 99:52230p, 1983.

Ferro, "Possible Enhancement of Endothelial Cell Function Induced by Defibrotide," Chemical Abstract (1988), 109:104533m.

Girard et al., "Multivitamin for Treating Herpes Infections," Chemical Abstract No. 96:168754e, 1982.

Gendelman et al., "A Selective Defect of Interferon α Production in Human Immunodeficiency Virus–Infected Monocytes," Chemical Abstract No. 113:170225w, 1990.

Marni, "Protection of Kidney from Postischemic Reperfusion Injury in Rats Treated with Defibrotide," Chemical Abstract (1991), 114:55511v.

Merck Index 11th Ed., 1990, p. 192 (#1244–13 Biotin) and 449 (#2851—Defibrotide).

Oral et al., "Staphylococcal Protein—A Immunoadsorption (SPA) and Profabirnolytic Agent Defibrotide (D) Therapy of Thrombotic Microangiopathy," *Blood, J. Amer. Soc. Hemat.*, Abstract 411a, Nov. 1989.

Wagner, "Applications of New Cyanine Labeling Reagents in Flow Cytometry," Abstracts for the XIV International Meeting of the Society for Analytical Cytology, Asheville, N.C., Mar. 18–23, 1990, 459A.

Berti, et al., "Opposite Effects of PGI$_2$ and PAF Generated During Acute Myocardial Ischemia in the Perfused Rabbit Heart," *Adv. Prost. Thromb. & Leuk. Res.*, 21:939–942 (1990).

Bilsel, et al., "Interaction of $^3$H–Defibrotide with Cultured Human Umbilical Vein Endothelial Cells," *Thromb. Res.*, 58:455–460 (1990).

Bloom et al., "Tuberculosis: Commentary on a Reemergent Killer," *Science*, 257:1055–1064 (1992).

Bonomini, et al., "Effect of a New Antithrombotic Agent (Defibrotide) in Acute Renal Failure Due to Thrombotic Microangiopathy," *Nephron*, 40:195–200 (1985).

Bonomini, et al., "Use of Defibrotide in Renal Transplantation in Man," *Haemostasis*, 16:48–50 (1986).

Chaiet, et al., The Properties of Streptavidin, A Biotin–Binding Protein Produced by *Streptomycetes, Arch. of Biochem. and Biophys.*, 106:1–5 (1964).

Cirillo, et al., "In vitro Inhibition by Defibrotide of Monocyte Superoxide Anion Generation: A Possible Mechanism for the Antithrombotic Effecti of a Polydeoxyribonucleotide–Derived Drug," *Haemostasis*, 21:98–105 (1991).

Cizmeci, et al, "In vivo Effects of Defibrotide on Platelet c–AMP and Blood Prostanoid Levels," *Haemostasis*, 16:31–35 (1986).

Coccheri, et al., "Effect on Fibronolysis of a New Antithrombotic Agent: Fraction P (Defibrotide). A Multicentre Trial," *Int. J. Clin. Pharm. Res.*, 11:227–245 (1982).

Coccheri, et al., "Defibrotide," *Cardiovascular Drug Rev.*, 9:172–196 (1991).

Colman, et al., "Antisense Strategies In Cell and Development Biology," *J. Cell Science*, 97:399–409 (1990).

Cornelli, et al., "Defibrotide: An Overview of Clinical Pharmacology and Early Clinical Studies," *Seminars in Thromb. & Hemostasis*, 14:64–70 (1988).

Costantini, et al., "Effects of Defibrotide on Prostanoid Synthesis and Fibrinolytic Activity in Human Veins," *European J. of Internal Med.*, 1:115–120 (1989).

Dauber, et al., "Flow Cytometric Analysis of Lymphocyte Phenotypes in Bronchoalveolar Lavage Fluid," Dept. of Biological Science, The Mellon Institute, Carnegie–Mellon University, Pittsburgh, PA, (1991).

Fareed, et al., "Pharmacologic Validation of the Antithrombotic and Vascular Effects of Defibrotide," *Adv. in Vascular Path.*, 171–177 (1990).

Fareed, et al., "Pharmacologic Profiling of Defibrotide in Experimental Models," *Seminars in Thromb. and Hemostasis*, 14:27–37 (1988).

Fauci, "Multifactorial Nature of Human Immunodeficiency Virus Disease: Implications for Therapy," *Science*, 262:1011–1018 (1993).

Gao, "Mechanisms of Inhibition of Herpes Simplex Virus Type 2 Growth by 28–mer Phosphorothioate Oligodeoxycytidine," *J. Biol. Chem.*, 265:20172–20178 (1990).

Green et al., "Optical Rotatory Dispersion, Circular Dichroism and Far–Ultraviolet Spectra of Avidin and Streptavidin," *Biochem. J.*, 100:614–621 (1966).

Green, "Avidin," *Adv. Prot. Chem.*, 29:85–133 (1975).

Gryglewski et al., "Prostacyclin and the Mechanism of Action of Defibrotide," *Eicosanoids*, 2:163–167 (1989).

Helene et al., "Specific Regulation of Gene Expression by Antisense, Sense and Antigene Nucleic Acids," *Biochimica et Biophysica Aeta*, 1049:99–125 (1990).

Horn et al., "Biotin–Mediated Delivery of Exogenous Macromolecules into Soybean Cells," *Plant Physiol.*, 93:1492–1496 (1990).

Leonetti et al., "Intracellular Distribution of Microinjected Antisense Oligonucleotides," *Proc. Natl. Acad. Sci.*, 88:2702–2706 (1991).

Leonetti et al., "Biological Activity of Oligonucleotide–Poly(L–lysine) Conjugates: Mechanism of Cell Uptake," *Bioconjugate Chem.*, 1:149–153 (1990).

Lobel et al., "Selective Stimulation of Coronary Vascular $PGI_2$ But Not of Platelet Thromboxane Formation by Defibrotide in the Platelet Perfused Heart," *Naunyn–Schmiedeberg's Archives of Pharmacol.*, 331:125–130 (1985).

Loke et al., "Characterization of Oligonucleotide Transport Into Living Cells," *Proc. Natl. Acad. Sci.*, 86:3474–3478 (1989).

Marni et al., "Protection of Kidney from Postischemic Reperfusion Injury in Rats Treated with Defibrotide," *Transplantation Proceedings*, 22:2226–2229 (1990).

McDougal et al., "Cellular Tropism of the Human Retrovirus HTLV–III/LAV," *J. of Immunology*, 135:3151–3162 (1985).

McDougal et al., "Immunoassay for the Detection and Quantitation of Infectious Human Retrovirus, Lymphadenopathy–Associated Virus (LAV)," *J. Immunol. Methods*, 76:171–183 (1985).

Miller et al., "Oligonucleotide Methylphosphonates as Antisense Reagents," *Bio/Technology*, 9:358–362 (1991).

Mitsuya et al., "Molecular Targets for AIDS Therapy," *Science*, 249:1533–1544 (1990).

Niada et al., "$PGI_2$–Generation and Antithrombotic Activity of Orally Administered Defibrotide," *Pharmacological Res. COmm.*, 14:949–957 (1982).

Niada et al., "Antithrombotic Activity of a Polydeoxyribonucleotidic Substance Extracted From Mammalian Organs: A Possible Link with Prostacyclin," *Thromb. Res.*, 23:233–246 (1981).

Niada et al., "Cardioprotective Effects of Defibrotide in Acute Lethal and Nonlethal Myocardial Ischemia in the Cat," *Haemostasis*, 16:18–25 (1986).

Nokta et al., "Human Immunodeficiency Virus Replication: Modulation by Cellular Levels of cAMP," *AIDS Res. & Human Retrov.*, 8:1255–1261 (1992).

Orloff et al., "Penetration of CD4 T Cells by HIV–1: The CD4 Receptor Does Not Internalize with HIV, and CD4–Related Signal Transduction Events are not Required for Entry," *J. Immunol.*, 146:2578–2587 (1991).

Pape et al., "Effect of Isonlazid Prophylaxis on Incidence of Active Tuberculosis and Progression of HIV Infection," *Lancet*, 342:268–272 (1993).

Pescador et al, "Pharmacokinetics of Defibrotide and of its Profibrinolytic Activity in the Rabbit," *Thromb. Res.*, 30:1–11 (1983).

Ross, "Twists and Turns on G–Protein Signalling Pathways," *Current Biol.*, 2:517–519 (1992).

Sabba et al., "A Pilot Evaluation of the Effect of Defibrotide in Patients Affected by Peripheral Arterial Occlusive Disease," *Intl J. Clin. Pharm., Ther. & Toxic.*, 26:249–252 (1988).

Sarin et al., "Inhibition of Acquired Immunodeficiency Syndrome Virus by Oligodeoxynucleoside Methylphosphonates," *Proc. Natl. Acad. Sci.*, 85:7448–7451 (1988).

Shea et al., "Synthesis, Hybridization Properties and Antiviral Activity of Lipid–Oligodeoxynucleotide Conjugates," *Nucl. Acids Res.*, 18:3777–3783 (1990).

Sullenger et al., "Overexpression of TAR Sequences Renders Cells Resistant to Human Immunodeficiency Virus Replication," *Cell*, 63:601–608 (1990).

Tatham et al., "FLow Cytometric Detection of Membrane Potential Changes in Murine Lymphocytes Induced by Concanavalin A," *Biochem.*, 221:137–146 (1984).

Tidd, "A Potential Role for Antisense Oligonucleotide Analogues in the Development of Oncogene Targeted Cancer Chemotherapy," *Anticancer Res.*, 10:1169–1182 (1990).

Ulutin et al., "The Pharmacology and Clinical Pharmacology of Defibrotide: A New Profibrinolytic, Antithrombotic and Anti–Platelet Substance," International Sciencific Symposium on Fibrinogen, Thrombosis, Coagulation and Fibrinology, Aug. 30–Sep. 1, 1989 Taipei, Taiwan, ROC.

Ultin, "Clinical Effectiveness of Defibrotide in Vaso–Occulsive Disorders and Its Mode of Actions," *Seminars in Thromb. and Hemost.*, 14:58–63 (1988).

Vangelista et al., "Effects of Defribotide in Acut Renal Failure Due to Thrombotic Microangiopathy," *Haemostasis*, 16:51–54 (1986).

*Primary Examiner*—Jeffrey Fredman
*Attorney, Agent, or Firm*—Banner & Witcoff, Ltd.

[57] ABSTRACT

Oligodeoxyribonucleotides, polydeoxyribonucleotides and derivatives thereof, such as defibrotide, are agents of genetic modulation at the levels of transcription, translation, secondary messengers and cellular signal transduction systems. Various disease states can be treated by modifying the dose of such agents in response to observed fluctuations (e.g., increase, decrease, appearance, disappearance) in normal, disease and repair markers.

25 Claims, 8 Drawing Sheets

METHOD FOR USING POLYNUCLEOTIDES, OLIGONUCLEOTIDES AND DERIVATIVES THEREOF TO TREAT VARIOUS DISEASE STATES

This application is a continuation-in-part of application Ser. No. 08/002,395, filed Jan. 13, 1993, now abandoned which is a continuation-in-part of the following U.S. Patent applications: application Ser. No. 07/748,277, filed Aug. 21, 1991, now abandoned application Ser. No. 07/815,130, filed Dec. 27, 1991, now abandoned and application Ser. No. 07/830,886, filed Feb. 4, 1992 now abandoned.

FIELD OF INVENTION

The invention relates to a method of using sequence non-specific polydeoxyribonucleotides, oligodeoxyribonucleotides and/or derivatives thereof, such as defibrotide, to treat various human disease states.

BACKGROUND OF THE INVENTION

Defibrotide is a polyanion salt of a deoxyribonucleic acid obtained from mammalian tissue. Defibrotide is a single-stranded polydeoxyribonucleotide with molecular weight of approximately 20 kDa (low molecular weight form) which may be obtained from bovine lung DNA by controlled hydrolysis. Patents related to its manufacture include U.S. Pat. No. 3,770,720 directed to a process for extracting DNA from mammalian tissue, and U.S. Pat. No. 3,899,481 directed to a process for the controlled partial degradation of DNA extracted from animal organs.

Defibrotide is noted primarily for its profibrinolytic effects (Pescador et al., 1985, *Thromb. Res.*, 30:1–11). Defibrotide increases the release of tissue-type plasminogen activator (t-PA) and decreases plasminogen activator inhibitor (PAI1) activity. The increase in t-PA is in conjunction with the decrease in PAI1, the latter being the more prominent action. The profibrinolytic activity of defibrotide is likely due to a decrease in PAI1 levels rather than to an increase in t-PA level (Pogliani et aL, 1987, *Farmaci E Therapia IV*, (2):1–5; Ulutin et al., *International Scientific Symposium on Fibrinogen, Thrombosis, Coagulation and Fibrinolysis*, Aug. 30–Sep. 1, 1989, Taipei, Taiwan, ROC).

U.S. Pat. No. 3,829,567 is directed to the use of an alkali metal salt of a polynucleotide or an oligonucleotide of ribonucleic acid (RNA) and/or deoxyribonucleic acid (DNA) as a fibrinolytic agent. U.S. Pat. No. 4,649,134 is directed to a method of treating acute renal insufficiencies accompanied by thrombotic microangiopathy with defibrotide. Such pathologies include hemolytic uremic syndrome (HUS), collagenopathies (e.g., panarteritis and lupus), Wegner, Schoenlein-Henoch, disseminated intravascular coagulation (DIC), fast evolving glomerulonephritis, and thrombotic thrombocytopenia purpura (TPP). U.S. Pat. No. 4,693,995 is directed to a method of treating acute states of myocardial ischemia and infarction with defibrotide.

While the primary target cell of defibrotide action has been shown in numerous studies to be the vascular endothelial cell (Bilsel et al., 1990, *Thromb. Res.*, 58:455–460), cytotropic actions have been shown for hepatic and myocardial cells as well (Lobel and Schror, 1985, *Naunyn-Schmiedeberg's Arch. Pharmacol.*, 331:125–130).

Defibrotide has been found to be a prostaglandin $I_2$ ($PgI_2$) secretory agent (Niada et al., 1982, *Pharmacological Res. Comm.*, 14:949–957). Defibrotide also induces synthesis of other prostanoid metabolites, such as prostaglandin $E_2$ ($PgE_2$). The increase in secretion of the prostanoid metabolites, in particular $PgI_2$ and $PgE_2$, from vascular endothelial cells seems to involve interaction with arachidonic acid metabolites (Costantini et al., 1989, *Eur. J. Int. Med.*, 1:115–120). It has been shown in rabbits that prostanoid neosynthesis induced directly by arachidonic acid was significantly enhanced by the stimulation of adenosine $A_1$ and $A_2$ receptors by defibrotide, especially at those levels that do not directly affect the output rate of $PgI_2$ and $PgE_2$ from the rabbit aorta vascular endothelial cells (Ulutin et al., *International Scientific Symposium on Fibrinogen, Thrombosis, Coagulation and Fibrinolysis*, Aug. 30–Sep. 1, 1989, Taipei, Taiwan, ROC). $PgI_2$ and $PgE_2$ promote microcirculatory vasodilation and antagonism of platelet aggregation. Defibrotide induces an in vivo increase in platelet cyclic adenosine monophosphate (cAMP) levels resulting in deaggregation of platelets and plasma prostanoid levels, as shown in humans (Cizmeci, 1986, *Haemostasis*, 16 (suppl. 1):31–35). Defibrotide does not increase levels of malonylaldehyde, thromboxane $A_2$, thromboxane $B_2$, $\alpha_2$-antiplasmin, or $\alpha_2$-macroglobulin activities.

Defibrotide is also known to exhibit antithrombotic actions (Niada et al., 1981, *Thromb. Res.*, 23:233–246). Defibrotide has been shown to elevate Protein CA and Protein CI levels, which affects antithrombotic action. The reported elevations in the levels of Protein CA and Protein CI are proposed to be via defibrotide's modulatory effects on the vascular endothelial cell-thrombomodulin levels. At the dose levels utilized thus far, it is devoid of anti-coagulant effects (Coccheri et al., 1982, *Int. J. Clin. Pharm. Reg.*, 11(3):227–245), and no clinical applicability as an anti-coagulant agent has been taught heretofore.

Defibrotide exhibits a synergistic action with, and potentiates the effect of heparin (Ulutin et al., *International Scientific Symposium on Fibrinogen, Thrombosis, Coagulation and Fibrinolysis*, Aug. 30–Sep. 1, 1989, Taipei, Taiwan, ROC). The synergistic mechanism between defibrotide and heparin is not totally clear. One proposed theory is that defibrotide competitively binds with heparin receptors, promoting prolonged circulation of endogenous heparin. Ulutin et al. reported an increase in anti-Factor Xa activity (Ulutin et al., *International Scientific Symposium on Fibrinogen, Thrombosis, Coagulation and Fibrinolysis*, Aug. 30–Sep. 1, 1989, Taipei, Taiwan, ROC). This effect may add to its antithrombotic action.

In a comparable animal model of the rat aortic strip, defibrotide was shown to inhibit endothelin-induced contraction of the vascular smooth muscle (Fareed et al., 1990, In: *Advances in vascular pathology*, Elsevier Science Publishers B. V., pp. 171–177). This implies that factors other than impaired fibrinolysis were being treated by defibrotide, such as defibrotide-induced suppression in the levels of the vasoactive amines secreted from the vascular endothelial cells in response to injury. In umbilical vein human endothelial cell cultures, defibrotide was shown to increase cell number and protein content in the culture supernatant, implying a greater role in translation than in the induction of mitotic activity (Bilsel et al., 1990, *Thromb. Res.*, 58:455–460).

Additional data on defibrotide reveals that defibrotide can modulate lipid peroxidation of membrane phospholipids and oxygen radical induced inhibition of the cyclooxygenase pathway, two major mechanisms in the process of vascular endothelial cell injury. Analogous to these are defibrotide-induced inhibition of superoxide generation by neutrophils induced from platelet activating factor (PAF) (Cirillo et al., 1991, *Haemostasis*, 21:98–105). Defibrotide has shown protective effect in mice against pulmonary embolism, analogous to the free radical scavenging enzymes superoxide dismutase and catalase (Niada et al., 1986, *Haemostasis*, 16 (suppl. 1): 18–25; Bonomini et al., 1985, *Nephron*, 40:195–200). Defibrotide-based antithrombotic action in pulmonary embolism may be analogous to the antioxidant effects of cardiovascular drugs.

The cytotropic effects of defibrotide are proposed to be on the basis of $PgI_2$-induced vasodilatation of the microvasculature and the secondary increases in the tissue oxygenation and nutrition. While it has been reported that defibrotide acts via modulation of vascular endothelial cells, its recently formally adopted pharmaceutical classification as a "polypharmaceutical agent" is uniformly ascribed to defibrotide's $PgI_2$ secretory action.

Pre-clinical and clinical experience with defibrotide as well as ex vivo and animal studies done over the past ten years in Europe evidences a cyto-protective effect in myocardial warm and cold ischemia (increased tissue ATP, ADP, 2-3DPG, NADP/NADPH levels), and in reperfusion injuries in the ischemic myocardium and liver (decreased lactate, CPK, intracellular pH), as well as organ procurement and transplantation, proving its cyto-protective effects in other cell types such as myocardial and hepatic cells (Niada et aL, 1986, *Haemostasis*, 16 (suppl. 1): 18–25; Berti et al., 1990, *Advances in Prostaglandin, Thromboxane, and Leukotriene Research*, 21:939–942). The anti-ischemic effect-induced salvage of the cellular energy pools were ascribed to adenosine receptor induced stimulation of adenylate cyclase enzyme pathway.

Defibrotide therapy has been used in disease states in which inappropriate production or intravascular deposition of fibrin has been a prominent factor. Peripheral obliterative vascular disease (POVD) comprises its primary commercial application in Europe (Ulutin, 1988, *Semin. Thromb. Hemost.*, 14(suppl 1):58–63), accompanied by the secondary clinical indications of prophylaxis of perisurgical deep vein thrombosis (DVI), and by its less well established use in hemodialysis. Clinical application has been investigated in vasculitides (Raynaud's disease (humans)), prolongation of graft survival in renal transplantation (humans), DIC (animal models), sepsis (animal models), stroke (animal models), renal failure and thrombotic microangiopathy (HUS, TrP humans)) (Bonomini et al., 1985, *Nephron*, 40:195–200; Vangelista et al., 1986, *Haemostasis* 16 (suppl. 1):51–54; Oral et al., 1989, *Blood* 74(suppl 1):41 11a). Defibrotide has been administered to humans primarily as an investigational agent in the United States.

Defibrotide is manufactured by CRINOS Farmacobiologica S.p.A., Villa Guardia (Como), Italy, and is currently marketed only in Italy. Defibrotide, obtained from CRINOS for investigational purposes and clinical trials in the United States, is available in ampules containing 200 milligrams for parenteral administration and in tablets containing 400 milligrams for oral administration.

Although verifiable data indicates that defibrotide, as a nucleic acid, is not toxic, mutagenic or harmful to fetal or embryonic development, maximum dosages of defibrotide administered to humans have been limited to either a body weight-dependent dose of 10–30 milligrams per kilogram, to an empirically established dose of 5.6 grams per day, intravenously, or a fixed dose of 800 milligrams per day, intravenously or by mouth. Coccoheri and Biagi (*Cardiovascular Drug Reviews*, 1991, 9(2):172–196) report the highest dose of 2.4 to 5.6 grams daily which was given for three days only. These doses, which were based on previous animal studies, were administered empirically. Defibrotide was administered in conjunction with conventional therapy and produced modest advantage.

The pharmacodynamic effect obtained with oral administration of defibrotide is approximately one-half that of parenteral dosing (Fareed et al., 1988, *Seminars in Thrombosis and Hemostatis*—Supplement, 14:27–37). The maximum dosages of oral defibrotide reported was 1600 milligrams per day. Even at these dosages, clinical improvement was much slower with the oral form of defibrotide than with the parenteral form.

Studies in human pharmacology have been conducted on the same nondynamic, merely descriptive, principles as the pre-clinical studies, i.e., merely confirming the molecular events induced by defibrotide at pre-determined, set dose levels, uniformly assessed on the principles of using a "minimum efficacious dose." In healthy volunteers, 1200 mg/2 hours was reported to induce increases in the levels of 6keto $PgF_{1a}$ and $PgE_2$ (not confirmed subsequently by other investigators) (Gryzlewski R. J. et al., *Eicosanoids*, 1989, 2:163–167), and 1200 mg/day for 2 weeks induced production of prostanoids and inhibition of arachidonic acid 5-lipoxygenase products, the latter known to contribute to pathogenesis and evolution of ischemic tissue damage.

The pro-fibrinolytic effect in healthy volunteers was confirmed by the administration of a single 400–600 mg dose with shortening only in euglobulin lysis time. Administration to peripheral obstructive vascular disease (POVD) patients in dose levels of 800 mg per day given orally, or 200, 400 and 800 mg per day given intramuscularly, displayed an additional effect of decreased PAI1 levels. Conversely, a more recent study failed to show significant activation of fibrinolysis in normal volunteers. A repeat study of POVD patients confirm significant defibrotide induced declines in PAIl levels (Coccoheri and Biagi, 1991, *Cardiovascular Drug Reviews*, 9(2):172–196). As a whole, the fibrinolytic effects in healthy volunteers were in general not reproducible, but in patients fibrinolytic effects were reproducible.

In direct opposition to its remarkable potentials in animal models and in vitro/ex vitro systems, published clinical studies with defibrotide have been notable for their modest-to-equivocal results in the respective areas of clinical application. One study continued intravenous defibrotide therapy for as long as three months ("Clinical Effectiveness of Defibrotide in Vaso-Occlusive Disorders and Its Mode of Actions", O. N. Ulutin, M.D. Thieme, Medical Publishers, Inc., *Seminars in Thrombosis and Hemostasis*—Supplement, Vol. 14, 1988). The majority of the remaining studies administered intravenous defibrotide for only two to three weeks, followed by the administration of oral defibrotide for a period of days to up to six months. Most studies ended at the discontinuation of defibrotide administration. Only one study followed patients for up to three years, although defibrotide was given for only three months ("Defibrotide: An Overview of Clinical, Pharmacology and Early Clinical Studies", Umberto Cornelli, M.D. and Marco Nazzari, M.D., Thieme Medical Publishers, Inc., *Seminars in Thrombosis and Hemostasis*—Supplement, Vol. 14, 1988). More recently, in a double-blind, randomized study conducted in peripheral arterial disease, defibrotide was administered orally for six months. Nearly all clinical studies (thus far) have focused on the agent's profibrinolytic and antithrombotic effects.

In summary, defibrotide has been shown in the art to have antithrombotic, thrombolytic, cytotropic, nephroprotective, platelet deaggregatory and anti-shock properties. These properties have been ascribed to its capacity to release $PgI_2$ or its stable analogues from vascular endothelium. Defibrotide has also been shown to increase t-PA, decrease PAII, increase protein S and C levels, increase ATIII (unconfirmed reports), increase platelet cAMP levels and, more recently, decrease endothelin-I levels and increase EDRF (endothelium derived relaxing factor) in in vitro models.

In all studies heretofore reported, a particular patient's condition was assessed by using the subjective and objective clinical signs and symptoms of the patient. To date, laboratory results, such as various coagulation assays have been used only to determine the safety and efficacy of defibrotide treatment but not to tailor the therapeutic dose to the individual patient's disease entity or the disease severity or response to prior treatment. Escalating dose levels were never attempted and/or evaluated. Rather, the art has assumed that side-effects will occur when defibrotide is administered in amounts exceeding the "minimum efficacious dose."

Moreover, the art has not recognized that alkali salts of deoxyribonucleic acid, such as defibrotide, may be useful in the treatment of vial infections, including HIV infection.

SUMMARY OF THE INVENTION

It is an object of the invention to provide a universal method useful in treating various disease states, including but not limited to vascular, cardiac, renal, viral, autoimmune and inflammatory disorders.

Another object of the invention is directed to a method of gene therapy for treating viral infections, such as the human immunodeficiency virus (HIV) without employing retrovirus, adenovirus or other viral vector.

To accomplish these and other objects, this invention provides a method of treatment comprising the steps of:

(a) determining the initial state of a set of disease markers, the disease markers being observable characteristics of a patient which deviate from the normal condition due to the disease state and wherein each disease marker in the set has a predetermined reference range which is indicative of the normal condition, (b) administering to the patient a dose of a therapeutic compound comprising one or more sequence non-specific nucleic acids selected from the group consisting of polydeoxyribonucleotides, oligodeoxyribonucleotides and derivatives thereof, (c) selecting a repair marker, the intensity of which increases following administration of the therapeutic compound, where intensity is the extent to which the state of the repair marker differs from its state in the normal condition, the repair marker being the concentration of a compound which participates in a cellular regulatory pathway which operates through protein kinase A, protein kinase C, or G-protein, (d) administering the therapeutic compound at a dose level incrementally higher than the previous dose, (e) repeating step (d) each time the intensity of the repair marker increases following an incrementally higher dose, (f) repeating steps (d) and (e) until the intensity of the repair marker in step (c) no longer increases, (g) administering the therapeutic compound at the highest dose level attained in step (f) until the intensity of the repair marker returns to the normal condition, and (h) administering the therapeutic compound at a dose level incrementally higher than the previous dose and repeating steps (c), (d), (e), (f) and (g) with one or more additional repair markers until all disease markers of said set of disease markers no longer deviate from the normal condition.

The patient is monitored weekly for three or more weeks. If relapse occurs, as indicated by a deviation of one or more disease and/or repair markers from the normal level, therapy is reinitiated at the highest dose level of the prior course of therapy until normalization is again reached.

In a preferred embodiment of the invention, the method of treatment comprises the steps of:

(a) determining the initial state of a set of disease markers, the disease markers being observable characteristics of a patient which deviate from the normal condition due to the disease state and wherein each disease marker in the set has a predetermined reference range which is indicative of the normal condition, (b) administering to the patient a dose of a therapeutic compound comprising one or more sequence non-specific nucleic acids selected from the group consisting of polydeoxyribonucleotides, oligodeoxyribonucleotides and derivatives thereof, wherein the dose of the therapeutic compound is at a level which raises a universal marker to at least five times its normal level, the universal marker being a constitutively expressed molecule which is transcriptionally activated by the therapeutic compound in all disease status, and (c) continuing to administer the therapeutic compound at the dose level of step (b) until the universal marker returns to its normal level.

In accordance with the invention, the treatment of viral diseases involves the administration of the therapeutic agent in the same marker dependent manner as indicated above. However, not only levels of those molecules misproduced by the normal cell, but also molecules produced by infected cells are assayed, e.g., viral encodal proteins. Cell cultures and other conventional tests are performed to detect the presence and activity level of virus and viral related components. The method includes titration of the dose to concurrently reestablish normal cell functions and neutralize and eliminate infectious viral particles.

The invention provides a method of gene therapy which comprises administration of combinations of (1) sequence specific nucleic acids corresponding specifically to selected parts of the viral genome or transcriptional factors and (2) sequence non-specific nucleotides, such as defibrotide and analogues thereof, in incrementally higher dose levels in a marker dependent manner.

The method of treating HIV infection or other viral disease according to the invention comprises the steps of administering an effective dose of one or more sequence non-specific nucleic acids selected from the group consisting of polynucleotides, oligonucleotides and derivatives thereof. Preferably, the method is practiced in a marker dependent manner comprising:

(a) determining the initial state of a set of disease markers, the disease markers being observable characteristics of a patient which deviate from the normal condition due to the disease state and wherein each disease marker in the set has a predetermined reference range which is indicative of the normal condition, (b) administering to the patient a dose of a therapeutic compound comprising one or more sequence non-specific nucleic acids selected from the group consisting of polynucleotides, oligonucleotides and derivatives thereof, optionally in combination with one or more sequence specific nucleic acids, (c) selecting a repair marker, the intensity of which increases following administration of the therapeutic compound, where intensity is the extent to which the state of the repair marker differs from its state in the normal condition, the repair marker being the concentration of a compound which participates in a cellular regulatory pathway which operates through protein kinase A, protein kinase C, or G-protein, (d) administering the therapeutic compound at a dose level incrementally higher than the previous dose, (e) repeating step (d) each time the intensity of the repair marker increases following an incrementally higher dose, (f) repeating steps (d) and (e) until the intensity of the repair marker in step (c) no longer increases, (g) administering the therapeutic compound at the dose level where the intensity of the repair marker no longer increases until the intensity of the repair marker returns to the normal condition, and (h) administering the therapeutic compound at a dose level incrementally higher than the previous dose and repeating steps (c), (d), (e), (f) and (g) with one or more additional repair markers until all disease markers of said set of disease markers no longer deviate from the normal condition.

The invention also provides a method of treating HIV infection in which HIV is not expressed and wherein the concentration of at least one immunological molecule is elevated above the normal level. Immunological molecules include CD4, CD25, IL-1, IL-3, IL4, IL6, TNF and sIL2R. The method comprises:

(a) administering to the patient an effective amount of a therapeutic compound comprising one or more nucleic acids selected from the group consisting of polynucleotides, oligonucleotides, and derivatives thereof, wherein the effective amount is the amount which causes a universal marker to rise at least five times its normal level, the universal marker being the concentration of a constitutively expressed molecule which is transcriptionally activated by the therapeutic compound in all disease states, and (b) continuing to administer the effective amount of the therapeutic compound until the universal marker returns to its normal level.

The invention is directed to the universal treatment of disease states characterized by the compromise and/or absence of normal cell functions. Treatment with therapeutic nucleic acid compounds, such as defibrotide, is universal in its application with respect to any disease condition wherein the diseased cell preserves the biological capacity for the physiologically predefined events of the recovery process. The decisive factor in the success of this therapeutic approach is not only the pharmaceutical agent itself, but how it is utilized. Treatment in accordance with the invention results in the activation of the inherent reparative cellular activity which will lead to the reinstitution of normal cellular functions. Revival or restoration of normal cellular functions is, by definition, a state of cure.

DETAILED DESCRIPTION OF THE INVENTION

Figure 1:
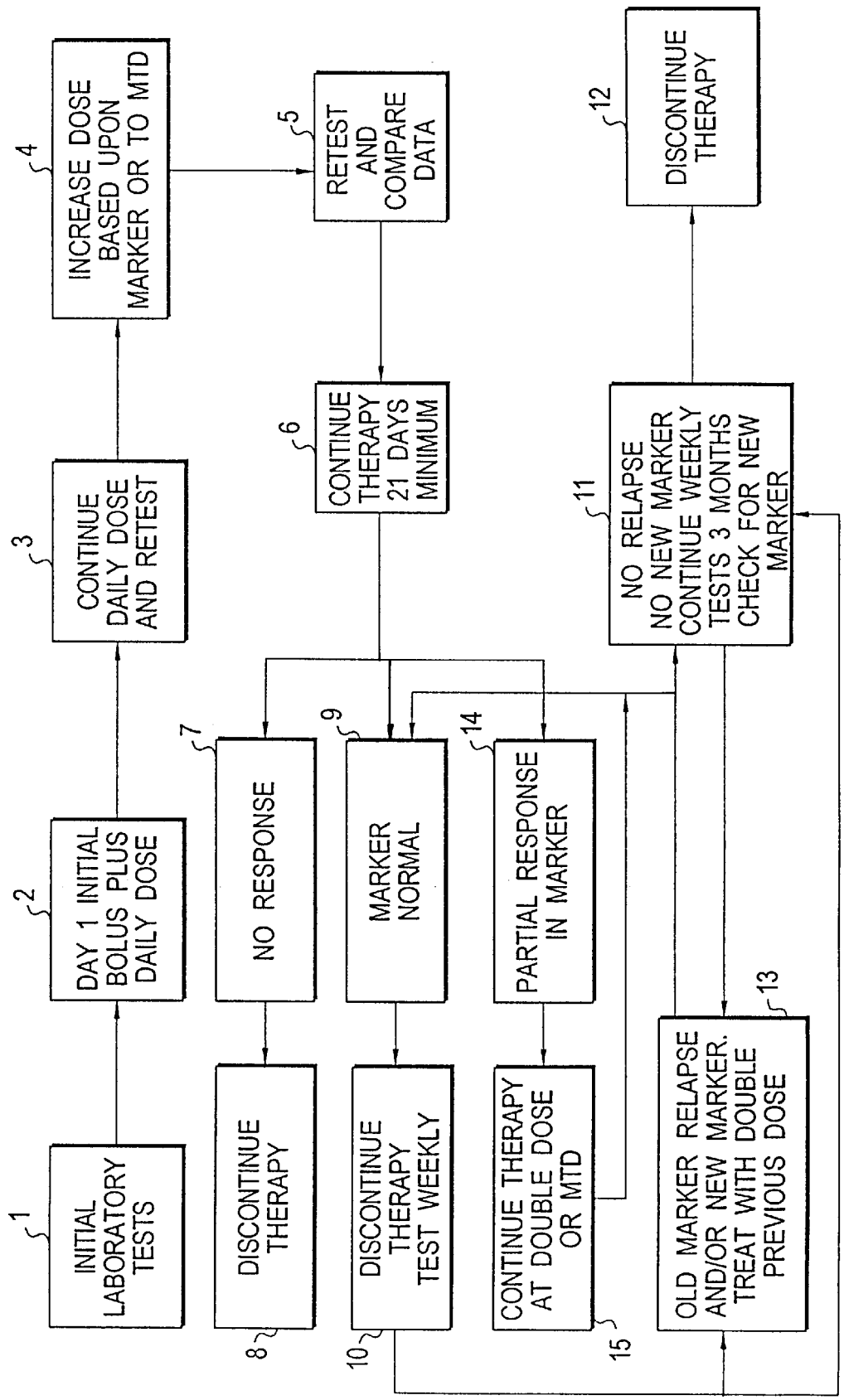
FIG. 1 is a diagram schematically illustrating the method of the invention.

This invention provides a method for the therapeutic multiphase application of therapeutic compounds which are polydeoxyribonucleotides, oligodeoxyribonucleotides, and/or derivatives thereof, including but not restricted to defibrotide, in the treatment of disease states, including HIV. It has now been discovered that therapeutic nucleic acids such as defibrotide can be used in a manner not heretofore employed in the art to manage vascular, cardiac, renal, viral, autoimmune, inflammatory, and other disease states in which the reparative cellular mechanisms and modulation of cellular genomes are induced.

It has unexpectedly been discovered that such agents are useful in the treatment of HIV including debilitating opportunistic secondary infections. Opportunistic secondary infections include herpes, cryptococcial diarrhea, scleroderma, arthralgia and tuberculosis.

HIV infection is characterized by a progressive decline in immune system function, suppressing the infected host's ability to overcome other, secondary infections. No cure has been found for HIV infection. The pathogenetic process in HIV infection is never unidimensional but, rather, extremely complex and multifactorial. The pathogenic progression may be only tangentially related to the direct infection of a given target cell. Fauci, 1993, Science 262:1011–1018. Death is inevitable, usually from an overwhelming secondary infection and/or HIV related neoplasm.

Current treatments for HIV infection attempt to retard the progress of the disease or relive symptoms. Treatments in use today include certain dideoxynucleosides such as azidothymidine (AZT or zidovudine, Burroughs-Wellcome), dideoxyinosine (ddI, Bristol-Myers Squibb) or dideoxycytidine (ddC, Hoffman-LaRoche). These agents can be toxic. Their applicability is limited because of the appearance in some patients of onerous, and sometimes lethal, side effects. These side effects include myelosuppression, peripheral neuropathy, and pancreatitis. In some patients, AZT has lost its effectiveness after prolonged use.

While many other drugs have been proposed for treatment of HIV infection, none have been demonstrated to be effective.

Mycobacterium tuberculosis, the agent of tuberculosis (TB) is a deadly pathogen. TB remains the leading cause of death in the world from a single infectious agent. While the risk of TB infection in the United States had been declining over the past century, the incidence of TB is now increasing.

The increased number of TB cases is attributable in part to the result of HIV and TB co-infection. *Science,* 1992, 257:1055–1064. AIDS patients often exhibit TB as a presenting opportunistic infection. TB occurring with HIV infection is a serious and growing public health problem. *The Lancet,* 1993, 342:268–272.

It has now been discovered that the administration of sequence non-specific DNA, such as defibrotide, decreases IL-1, IL-2, TNF-α and IL-6, all of which are known inducers of HIV proliferation. Administration of such an agent also increases total lymphocyte and T-lymphocyte counts, CD4 counts, and CD8 counts, as well as increasing cGMP/cAMP ratios to proportions seen in normal laboratory controls. An anabolic effect has also been observed.

Preferably, the deoxyribonucleic acid is administered in a marker dependent manner. A "marker" is an observable characteristics of the patient which may be observed directly by the clinician or determined by diagnostic procedures. The state of individual markers is correlatable with the status of disease or repair processes in the patient. Dosing of the therapeutic nucleic acids according to the method of this invention is based on changes in the status of these markers as taught herein.

Treatment of a disease state in accordance with this invention involves the administration of the therapeutic nucleic acids or derivative at a daily dose level sufficient to increase the intensity, determined as concentration or clinical observation, of a marker of cellular repair processes ("repair marker") to a plateau level (i.e., where the intensity of the marker is not changed by continued administration of the therapeutic compound). This daily dose level is the "maximum efficacious dose" for the particular disease and repair marker. Administration of the therapeutic compound is continued at the same dose level until the repair marker stabilizes by returning to the normal level.

If at least one disease marker remains in an abnormal state, the daily dose level of the therapeutic compound is increased. At least one other repair marker will increase in intensity, and the daily dose level is increased until the intensity of the new marker reaches a plateau level. Administration of the therapeutic compound is continued at this new maximum efficacious level until the respective repair marker stabilizes at the normal level.

When all disease markers have returned to the level of the normal state, administration of the therapeutic compound is discontinued, but the levels of the disease and repair markers are monitored every three weeks, for an additional 3–6 months. If the levels of all markers remains at that of the normal state, cure has been achieved. If any marker deviates from normal at the end of any three week period, administration of the therapeutic compound is resumed at the highest "maximum efficacious dose" that has been used during the immediate prior treatment, and the new maximum effective dose is established by the known methodology.

A system of dose assessment and completely new dose levels based on the concepts herein discussed has now been developed. First, since therapeutic nucleic acids such as defibrotide act to revive normal cell function, dose and duration of therapy must be modified individually per patient or disease depending on the function, type, and degree of cell injury. Second, defibrotide and other nucleic acids are cell modulators. In this regard, nucleic acids such as defibrotide and derivatives thereof have now been recognized by the inventor as the only class of agents committed to restoration of normal cell function. In itself, this effect of the therapeutic compound is incompatible (in a state of cure) with an "over-functional" state, i.e. any complications caused by the therapy. Hence, dose levels higher than the "minimum efficacious dose" used in the prior art will be complication free. Third, defibrotide has now been recognized to be a member of a new class of pharmaceutical agents that will act via activation of respective cell functions with varying polypharmacological actions that are disease specific, induced by varying dose levels of defibrotide. Fourth, this class of agents have to be administered at escalating dose levels until and when maximum clinical benefit is observed. Therapy with these agents requires the development of the "maximum efficacious dose" principle for the assessment of therapeutic dose levels, thus eliminating the heretofore universally applied principle of "minimum efficacious dose." Fifth, this class of agents represent the only polypharmaceutical agents of their kind which exert their therapeutic effects not by their direct molecular actions, but by activating (in the diseased cell) the selected polypharmacological events of the recovery process.

"Pleiotropism" as used herein, is defined as the tissue and cell specific expression of cellular genomes via phosphorylation of the enzymes, via reinstitution of cell-surface receptor ligand interactions, protein kinase A and protein kinase C pathways as well as second messengers of cAMP, $Ca^{2+}$, diacylglycerol (DAG), and 1–3 phosphoinositol which may under- or over-regulate the genomic transcriptional/transitional activities.

The term "maximum efficacious dose" is defined herein as the daily dose rate, that will elicit, in nearly 100% of treated patients, the reversal of the respective disease markers to the uniformly normal level, and establishment of normal cellular markers. The maximum efficacious dose is usually expressed as amount of therapeutic compound administered per kilogram body weight per day (DKGD). The maximum efficacious dose represents a novel concept of administering a pharmaceutical agent in therapeutic medicine.

The term "maximum therapeutic dose" is defined herein as the total cumulative dose (the daily dose summed over the duration of administration) that will elicit in nearly 100% of treated patients the irreversible and complete normalization of the respective disease markers and resumption of normal cellular functions, i.e., the state of cure.

The term "minimum efficacious dose", is used herein to refer to the dose used in the heretofore universal practiced method of administering a pharmaceutical agent. The minimum efficacious dose is the dose (daily dose or steady state level) that will elicit a particular pharmaceutical action in a certain percentage of patients, without inducing the pleiotropism of the whole repair process.

Pharmacological agents have heretofore been administered at set dose levels (i.e., the "minimum efficacious dose") to treat the gross pathology and discontinued when complete or partial remission of the gross pathology was achieved. The object of the invention is to achieve complete remission of each disease stage. Treatment according to this invention begins at the gross pathology stage which has one or more associated markers. Normalization or improvement of those markers indicate that the treatment is beneficial. In conventional treatments of disease, treatment is stopped after a certain period of time at a set dose level, usually corresponding to complete or partial remission of the disease indicators of gross pathology. However, such a remission is not the event which causes discontinuation of therapy in accordance with this invention. Normalization of the markers of gross pathology indicates, rather, that a disease state corresponding to a lower level of disease activity has been reached. Markers of that stage (i.e., the lower level of disease activity) are identified and treatment is continued to normalize those markers. Complete cure is reached only if all stages of the revival process are treated.

The term "maximum tolerable dose," as used herein, is defined as the highest daily dose that can be administered without any complications, e.g., no bleeding complications or thrombopathy, etc. This in fact has been the sole and primary side effect of the high-molecular weight nucleic acid (defibrotide) utilized in the studies reported herein, i.e., the antithrombotic effect inducing bleeding complications at 300 mg/kg/day dose or above. If the maximum efficacious dose should be higher than the maximum tolerable dose, chemical modification of the nucleotide for more efficacious transmembrane transport and cellular entry would be necessary.

The inventor has determined that the therapeutic nucleic acid will not indefinitely increase transcriptional activity with increasing doses. In this regard, transcriptional activity will shut off when the repair molecules are no longer needed, i.e., when no more "injury signal" is transmitted via stimulation of adenylate cyclase, second messengers, etc. In contrast, no matter how high the dose range in the normal individual may be, there is no induction of transcriptional activity (as indicated by, e.g., elevation in the von Willebrandt antigen (vWAg) levels). This supports the fact that no complications are seen with therapy using nucleotides which modulate cellular repair mechanisms for a therapeutic effect. For example, tissue plasminogen activator antigen (AgTPA) will not continue to rise indefinitely with increasing doses but will increase only in the presence of injury and at the locality of the injury, e.g., the existence of a thrombus which inevitably will be associated with the endothelial cell of the locality specific lesion. Hence no bleeding complications are to be seen secondary to systemic induction of the therapeutic compound at physiological dose ranges beyond the upper limits of the prior art thrombolytic therapy.

This mechanism is supported by the way the cell modifies activation of the repair process. As is well known, 50% occupation of cell surface receptors will lead to 50% increase in the baseline level of intracellular cAMP, 100% occupation of cell surface receptors will lead to a 100% increase in the intracellular cAMP level. This will correspond to 5 times the elevation of the baseline vWAg level. As shown by FIGS. 2–9, the projected rise in the levels of vWAg and AgTPA over the previous dose range becomes negligible beyond 5 times the elevation over the baseline.

Phosphorylation of various different transcriptional factors simultaneously will lead to concurrent tissue specific turning on or off of the respective transcriptional factors, e.g., some molecules are turned on and some are turned off. This constitutes the pleiotropism of the nucleic acids as herein defined.

Treatable Disease States

The disease states treatable by the method of this invention are those characterized by injury-based alteration in the production, expression or activity of compounds whose production, expression or activity is regulated by the cell at least in part through cell surface receptors such as Adenosine $A_1$ and $A_2$, collagen, thrombin, epinephrin and norepinephrine receptors, through the protein kinase A or protein kinase C pathways, or by protein factors whose phosphorylation affects genomic translation and transcription. The disease states treated by the method of this invention may have an abnormal genomic component.

Diseases with an abnormal genomic component are characterized in that one factor in the disease process is the expression of an abnormal DNA sequence related to the disease. Such sequences may include viral genomes, transformed genes such as activated oncogenes, or heritable genetic defects associated with genetic diseases. While the method of this invention will result in the return of normal cellular function in the diseases with an abnormal genomic component, a complete cure as defined herein will not remove the abnormal DNA sequence solely by administration of the therapeutic nucleotide compound. As taught herein, the preferred method for treatment of disease states with an abnormal genomic component contemplates adding to administration of the therapeutic nucleotide compound a coupled treatment directed at eliminating disease-related DNA sequences, for instance by removing the genomic defect.

Diseases with no abnormal genomic component are those diseases within the broad definition of diseases treatable by the method which do not involve expression of an abnormal DNA sequence. Complete cure can be achieved in diseases with no abnormal genomic component solely by administration of the therapeutic compound as described herein. It is within the contemplation of this invention to administer the therapeutic compound either alone or contemporaneously with other therapy directed to the particular disease process. It should be recognized that the other therapies are intended to force non-normal cellular function, and therefore they are likely to extend the time required for therapy with the therapeutic nucleotide compounds to achieve a return to normal cellular function.

Disease states involving cell malfunction of, for example, vascular endothelial cells, the cellular components of parenchymal tissue damage involving the kidney, heart, liver, etc., any disease state involving malfunctioning of the blood vessels, circulating blood cells, disease states of the central, peripheral and autonomic nervous systems and viral diseases involving reversible genetic modulation of the immune cells not excluding infestation of the tissue cells of the. involved organs may be treated with defibrotide and its derivatives. Such diseases include, but are not limited to POVD, DVT, DIC, thrombotic microangiopathies (e.g., HUS, TTP); renal failure; nephrogenic hypertension; consumptive thrombocytopenia, acquired thrombopathy and hemolysis; immunosuppression; autoimmune diseases such as rheumatoid arthritis; post-phlebitic syndrome; tissue necrosis with or without proximal vascular occlusion; acute/subacute (subendocardial) myocardial infarction; adult respiratory distress syndrome (ARDS); thrombosis of cranial sinuses; ischemic parenchymal tissue damage; acute myocardial infarction; pulmonary embolism; thrombotic cerebrovascular events; vascular endothelitis (e.g., Kawasaki's disease, polyarteritis nodosa, midline granuloma); scleroderma, Raynaud's disease; inflammatory (autoimmune or otherwise) myositis; inflammatory dermatitis; inflammatory symptoms of systemic lupus erythematosus (SLE) and other collagen vascular diseases; Sjogren's disease; inflammatory bowel disease (IBD); thyroiditis; stasis ulcers; sickle cell disease; pulmonary fibrosis; hypersensitivity pneumonitis; burns; peripheral obstructive arterial disease; septic shock; eclampsia; graft vs. host disease; retroviral diseases including HIV infection, adenoviral; herpetic and other viral infections; hyperimmune states such as chronic fatigue syndrome, solid organ rejection, venoocclusive disease, etc. Since prior art has shown the up-regulation of adenosine $A_1$ and $A_2$ receptors by defibrotide in the nerve cells, it can be inferred that the prototype nucleotide defibrotide and its derivatives may also be therapeutically beneficial in treating diseases of the nervous system.

The methodology described herein has universal application within the scope of disease states characterized by the absence or inadequacy of one or more of those cell functions which are normally regulated through the cell surface receptors listed above, through the protein kinase A or C pathways or by protein factors whose phosphorylation affects gene transcription, so long as the abnormalities in these cell functions are yet still reversible. The methodology is also applicable to the disease states characterized by acquired or genetic dismodulation, and/or transformation. Revival, institution or reinstitution of the normal state of those functions is, by definition, a state of cure. Revival of the normal cell functions can occur where the diseased cell preserves the biological capacity for the physiologically predefined events of the cellular repair functions of the recovery process, if those events are pharmacologically induced by the correct use of the therapeutic nucleic acids. Complete cure is the therapeutic objective. The decisive factor in the success of this therapeutic approach is not only the pharmaceutical agent, but how it is utilized. If the biological capacity for regaining normalcy is there, therapeutic failure is eliminated. This biologically predetermined potential for cure is reproducibly and predictably obtainable, however, only by the correctly determined iatrogenetically controlled dose levels, and duration of therapy. Incorrect dose administration leads to the therapeutically missed event of complete cure. Complete cure, however, is not possible if necessary dose levels cannot be attained without complications such as bleeding or thrombopathy.

Therapeutic Compounds

The invention uses polypharmacological medical therapy components which are defined by the predetermined biological events of the cellular repair process. The invention defines a previously unidentified class of drugs whose pharmaceutical actions modulate selectively and most effectively the injury specific cellular functions. This class of drugs include defibrotide as well as other nucleic acid derivatives. The pharmaceutical action is guided by the intrinsic biological material of the cell matching specifically and completely the cellular events of the recovery to the exact components of the injury.

The therapeutic compound contemplated for treatment by the method of this invention is an oligomer or a polymer of deoxyribonucleotides or ribonucleotides, or a derivative thereof. The compound may be native or chemically synthesized, or a fragment of a native polynucleotide. The compound has at least three nucleotide residues, and may have up to about 250 residues. Preferably, the nucleotide compound will have from about 15 to about 200 residues, more preferably from about 20 to about 150 residues, most preferably from about 50 to about 75 residues. The sequence of the nucleotide residues in the polymer is not critical, and may include sense, anti-sense, non-sense or missense sequences. A therapeutic composition may contain polynucleotide molecules with varying numbers of residues within the range described above. The skilled worker will be able to select an appropriate length (degree of polymerization) based on the ability of the compound to penetrate the cell and on the ability of the compound to cause a change in the level of various repair markers in accordance with the method of this invention.

The nucleic acid compound will preferably be relatively resistant to ecto- and endonucleases. The 3' OH of the terminal residue of the therapeutic compound according to this invention may be phosphorylated or not, and the compound will still function without the need for intracellular phosphorylation. The therapeutic compound according to this invention is a polyanion, and the negative charge is balanced by counter ions. The counter ions may be alkali metal ions or alkaline earth ions, biologic amines or other suitable counter ions which do not interfere with treatment according to the method of this invention. Preferably, at least some of the counter ions are zinc ions. Commercially available defibrotide contains about 150–350 µg of zinc and about 25–45 µg of iodine per gram of iodine. Zinc may be present in the nucleotide compound at a ratio of from 2–20 zinc atoms per phosphate group or iodine atom. Zinc containing compounds may be co-administered with the defibrotide to reach any desired ratio.

Defibrotide is chemically characterized as a polyanionic derivative of deoxyribonucleic acid. While further discussion will be directed to the use of defibrotide as the prototype drug, it is to be understood that other nucleic acids and derivatives are included in the use thereof. Derivatives included within the scope of the invention include nucleic acid, i.e., DNA and/or RNA, which is conjugated with poly(L-lysine) or which is modified by, for example, the addition of amino acids such as lysine, histidine and arginine, the addition of optimum concentrations of folate and/or biotin, the addition of the optimum ratios of metals and ions including zinc, manganese and iodine, by the addition of 5'-polyallyl moieties, cholesterol, vitamin E, 1-2-di-O-hexadecyl-3-glyceryl and other lipophilic moieties and/or modified by the replacement of phosphodiester bonds with phosphothiotate bonds, and/or modified nucleotide sequences of the prototype nucleic acid, defibrotide.

Verifications of the relative therapeutic unimportance of defibrotide's molecular structure in directly producing its various polypharmacological actions was provided by various means. These included non-uniformity of its various actions in different disease states; differences between the types of various "disease markers" reproducibly and effectively treated by defibrotide; lack of uniformity in the states of responsiveness of the same "disease markers" to the same "dose levels" at different stages of the disease process confirming greater responsiveness of the disease markers to lower dose levels with higher disease activity states and vice versa. This supports the concept that defibrotide's polypharmacological profile is a function of the injury state. The efficacy and the emergence of selected polypharmacological spectrum of actions, in turn, is a direct function of adequately administered dose levels.

While the inventor does not wish to be bound to a particular theory with respect to the mechanism of action of defibrotide, it is believed that treatment with defibrotide leads to the direct modulation of second messenger molecules such as cAMP, cAMP dependent protein kinase A enzymes, adenylate cyclase, G-proteins, the modulation of balancing signal transduction systems of calcium and diacylglycerol pathway, phosphoinositol, and protein kinase C enzymes as well as to the modulation, via cAMP, of phosphoproteins of transception and translation and cAMP modulated oncogenes such as c-myc, ras, c-fos, c-jun, NK-KB, transcriptional factors and lymphokines such as EIAI, AP-1, COUP, IL-2, IL6, TCF-1α, TATA, and TAT element, and oxygen radical modulation of cAMP response element (CRE) and modulation of CREB and CREM genes, as well as phosphoproteins of transcriptional and transitional cellular functions via protein kinase A/C induced phosphorylation of the respective enzymes.

As shown by the data presented herein, derivatives of nucleic acids, such as defibrotide, act upon malfunctioning cells to restore normal cell function. For a given disease certain cell malfunctions may be caused by the disease while other cell functions are normal. Only the malfunctions of the cell will be affected by treatment with defibrotide. Normal functions will not be hindered and/or increased during treatment.

The process of complete cure moves progressively from gross healing at the tissue level to healing at the molecular level, and thereafter, to healing at the genomic level. In order to accomplish a complete cure, therapy must be at the proper maximum efficacious dose and of the proper duration (i.e., maximum therapeutic dose) to eliminate the disease marker, fully induce the repair marker to completion of the repair process, and reinstate the normal cellular marker. Each successive stage of the repair process involves the dose management of all three marker classifications concurrently.

Marker-Driven Therapy

The claimed method involves the use of a "marker dependent dose assessment" methodology for determining the therapeutically most efficacious use of the respective pharmaceutical agents. The use of incremental marker stratification reflects the concept that "maximum efficacious dose" is redefined through the different stages of treatment, each time adjusted to the respective specific marker most representative of the respective pathogenic/clinical picture of the disease state. Treatment at respectively higher doses corresponding to the progressively lower disease activity levels are continued until a state of total cure is reached.

Intrinsic to the claimed method is the total elimination of empirically assessed doses or constant therapy doses, arrived at by the universal pharmaceutical principal of "minimum efficacious dose" for a class of drugs, which, until the present time, has been the standard for the definition of the "effective therapeutic dose." The respective doses thereof are defined to elicit a response corresponding to different disease functions of the treated cell and revival of the respective disease parameters, in a stratified fashion.

The method of treating various diseases provided by this invention uses specific clinical and laboratory markers to assess dosages to be administered. The markers vary from gross clinical observations of pathology to the progressively subclinical yet valid detection of certain laboratory levels associated with a particular disease. The preferred markers are the clinical parameters as well as the molecular products produced, or inhibited, present or absent when cellular events associated with a particular disease occur.

Certain laboratory assays are used to assure that the dosages are safe for the patient being treated. For therapy with defibrotide these may include prothrombin time, activated partial prothromboplastin time, thrombin time, reptilase time, bleeding time, platelet function assays, and coagulation factors. A second set of laboratory assays (i.e., "disease markers") are utilized to indicate the efficacy of the doses. "Repair markers" are used to assess clinical adequacy of dose escalation and duration of therapy.

As defined herein, "normal cellular markers" are molecules of normal cellular function. They are tissue and cell specific and may share common pathways of second messengers or signal transduction pathways and normal cellular genomes. At the genome level, normal cell markers are genes that are constitutively expressed, transcribed, translated and transduced. Establishing dose and duration of therapy based on second messengers, signal transduction pathways and induction of genomic transcription is a novel modality of administering a pharmaceutical agent.

As defined herein, "disease markers" are markers which are induced and defined by the type of disease process. Disease markers are clinical or laboratory parameters that deviate from normalcy. A disease marker may be absent or present, decreased or increased. At the genome level, disease markers are genomes of genetic dismodulation (e.g. viral genome, transcribed oncogenes, mistranscribed genomes); nontranscribed genomes (e.g., familial/genetically absent genomes, under-regulated/suppressed genomes), and/or overexpressed, not appropriately shut off transcriptions of genomes (e.g. activated repair molecules, second messengers and molecules of signal transduction pathways). Preferred disease markers for specific disease states are described herein.

Disease markers are observable characteristics of the organism whose status in a disease state differs from the status in the normal (non-disease) state. Such characteristics and their association with their respective disease states are well known to the skilled practitioner. In the practice of the method of this invention, it is contemplated that the practitioner will monitor the status of multiple disease markers related to the disease being treated, either simultaneously or sequentially.

The disease markers include both clinical markers, which are observed directly by clinician, and laboratory markers, which represent quantitative values determined by support staff. These characteristics include, but are not limited to, the concentration of compounds whose production or expression is affected by injury-based alteration of cell surface receptors such as Adenosine $A_1$ and $A_2$, collagen, thrombin, epinephrin and norepinephrine receptors, of protein kinase A or protein kinase C pathways, or of protein factors whose phosphorylation affects genomic translation and transcription, or hybridization of genomic enhancers/inhibitors infusion or excess enhancers, infusion of excess genomes to deplete viral/cellular transactivation transcription factors, etc. where the concentration in the disease state differs from the concentration in the normal state. The normal state concentration of these markers will be known to the skilled practitioner, and usually represents a range of concentration values determined by measurement of the concentration of the compound in a large number of individuals who are not in a disease state, by the respective laborator(ies).

Repair markers are compounds that participate in the regulatory pathways which include protein kinase A or protein kinase C. Adenylate cyclase is known to be activated by G-proteins (see Ross, 1992, Current Biology, 2(10) :517–519, the disclosure of which is incorporated herein by reference) with eventual production of cAMP and cAMP-dependent activation of protein kinase A, leading to phosphorylation of the respective transcription factors, until 100% of the cell membrane receptors are taken up by the ligands. For defibrotide these receptors are β-adrenergic receptors, collagen receptors, adenosine $A_1/A_2$ receptors, ADP receptors, thrombin receptors, collagen receptors, etc). A parallel pathway operates through activation of protein kinase C, in response to intracellular calcium ion level, inositol triphosphate and diacylglycerol, responsive to ligand binding to another set of receptors and similarly controlling transcription/translation of respective proteins. These pathways, and their intermediate compounds are well known to those skilled in the art. In particular, "repair markers" are molecules in the pathways of the respective cellular repair processes defined by the type of injury. Repair markers are transcribed or shut off genes, second messengers and/or molecules of the signal transduction pathways that may be increased, decreased, or absent in response to cellular injury. As discussed herein, the term "repair marker" may refer to the compound or its concentration or the measurement value of an assay associated with the concentration of the compound. The level of a repair marker may deviate from the level present in the cell during normal function, and when it does so deviate, cellular repair processes are activated. This deviation may be positive or negative, depending on the disease state and the precise state of cellular repair currently in progress. As discussed herein, the "intensity" of the repair marker will refer to the degree of deviation from the level during normal cellular function, without regard to whether the deviation is positive or negative. The use of repair markers in establishing dose and duration of therapy is a novel mode of administering a pharmaceutical agent.

As defined herein, a "universal marker" is a constitutively expressed molecule transcriptionally activated by the respective nucleic acid universally in all disease states for which the nucleic acid is specific. "Universal markers" are specific for each nucleic acid employed. While the universal marker is the only molecule that is not injury specific and has no therapeutic value, it is expressive of the event and duration of the ongoing repair process. Transcriptional activation gets shut off with the establishment of the state of cure. As such, the universal marker does not get modulated unless there is a disease state and the respective nucleic acid has therapeutic specificity. The universal marker carries a direct quantitative relationship to the daily per kilogram body weight dose (DKGD) of the nucleic acid employed. The universal marker defined for the prototype nucleic acid (defibrotide) is vWAg. Other "housekeeping genes" related to particular nucleic acids can be selected as per the target cell involved from the respective "housekeeping genes."

Clinical and clinical laboratory markers may be determined through blood tests, urine tests, clinical observation or identification of blood clots by any of several conventional techniques, as well as the more novel techniques of determining genomic transcriptional and transitional activity by DNA finger printing, PCR and the like. To evaluate the markers, the laboratory analyses measure levels of certain proteins, lymphokines, enzymes and relevant molecules. Clinical markers include blood pressure, visible tissue damage, signs of inflammation, ecchymoses, and the like. Clinical markers vary from one disease to another. Moreover, many diseases progress through several clinical stages during the process of recovery. The clinical markers of one stage of a disease are frequently different from the clinical markers in other stages of the disease, befitting different stages of the pathogenic picture.

The detection of markers relevant to the particular disease, stage of that disease, and as baseline for dose escalation, must first be identified. Any observable characteristic generally accepted by the skilled practitioner as being associated with a specific disease state may be employed as a clinical marker. See, e.g., Harrison's PRINCIPLES OF INTERNAL MEDICINE, 10th Edition, Petersdorf et al. Eds., McGraw Hill.

The normal state concentration of these markers will be known to the skilled practitioner, and usually represents a range of concentration values determined by measurement of the concentration of the compound in a large number of individuals who are not in a disease state, by the respective laboratory. While the skilled artisan would readily recognize those markers indicative of a pathological state, the following list is provided as a guideline.

Panel 1: Baseline Coagulation Panel for all Disease States
  Prothrombin time (PT)/PT Mix;
  Activated partial prothromboplastin time (APT T)/APTT Mix;
  Thrombin time (THR)/THR Mix;
  Reptilase time;
  dRVV/dRVV Mix (snake venom);
  TTI 1:5, 1:500;
  FIB.K, FIB.ACL, FIIA, V, VIII:C;
  von Willebrandt antigen (vWAg);
  anti-Factor FXa, FXI, FXIII;
  Platelet C, Platelet ADM;
  Clot retraction;
  Serum prothrombin time (SER PT);
  Bleed time;
  Platelet aggregation with ADP 20 (20 $\mu$g Adenosine diphosphate), ADP 5 (5 $\mu$g ADP), collagen, thrombin, epinephrin and arachidonic acid.

If PT, APTT, or THR are abnormal, the following assays should be included:
  F II, F V, F VII, F X, F IX, ETH GEL, PROT GEL, FDP (LATEX), FDP (STAPH), D-DIMER, and SER PT.

In addition to the baseline coagulation panel, the following assays should be conducted for the designated disease states:

Panel 2; Repair Marker (Signal Transduction Pathway) Panel (Intracellular in the target cell, such as platelets, peripheral blood mononuclear cells)
  Cyclic AMP (endogenous and PHA stimulated);
  assay is to be run in all the disease states along with the coagulation panel, along with vWAg (preferably messenger RNA of pro vWAg by PCR);
  cGMP (endogenous and PHA stimulated);
  gluthatione;
  GTP/GDP ($\gamma$-quinosine triphosphate/y-glutanyl diphosphate);
  GAP;
  RpAI (small G-protein);
  Gs 1 Alpha/Gi 1 Alpha;
  Gs 1 Alpha/Gi 1 Alpha (Activated G-protein/Inactivated G-protein ratio);
  oxygen radicals;
  NADP/NADPH ratio;
  FAD/FADH$_2$ ratio;
  intracellular Ca$^{2+}$ (endogenous, Interleukin 2 stimulated, PHA stimulated);
  intracellular 1,2 diacylglycerol (endogenous, IL-2 stimulated, PHA stimulated);
  intracellular inositol triphosphate (IP$_3$) (endogenous, IL-2 stimulated, PHA stimulated);
  adenylyl cyclase;
  protein kinase A;
  protein kinase C;
  Nf-kb.

Panel 3: Antithrombotic Marker Panel
  Protein CA;
  Protein CI;
  Protein SI;
  Protein ST;
  O$_2$-radicals by chemiluminescence;
  intracellular Ca$^{2+}$;
  calmodulin.

Panel 4: Profibrinolytic Marker Panel
  AgTPA;
  AgPAI1;

AgPAI3;
FPAI1.
Panel 5: Proplatelet Panel (for "Antiplatelet Therapy" with Concurrent
Antithrombotic Action via Prostanoids):
Intracellular $Ca^{2+}$;
cAMP (intracellular);
Platelet Factor 4;
β-TG, (glycoprotein 1 beta) (GP 1β);
collagen/arachidonic acid stimulated ATP secretion;
stimulated TMA 2 release;
mRNA/$PgI_2$ homologous desensitation to arachidonic acid;
platelet activating factor (1-0-hexadyl PAF);
plasma 6-keto $PgE_{1\alpha}$ (a $PgI_2$ metabolite);
b 6-keto $PgF_{1\alpha}$, 13-HODE (PMN); and
6-keto PgE 1/5 HETE (ratio);
platelet aggregations (with ADP 20, ADP 5, collagen, thrombin, epinephrin, arachidonic acid);
bleeding time.
Panel 6: Anti-inflammatory Panel (Rheumatic, Autoimmune, Burns, Radiation Injury)
IL-1;
IL-6;
soluble Interleukin 2 receptor (sIL2R);
α-interferon (γIFN);
TNF;
$\alpha_1$-antichymotripsin;
haptoglobin;
fibrinogen;
albumin;
lactoferrin;
metallothionein (hepatocyte);
catalase (liver enzyme);
fatty acid synthetase;
sialyltransferase;
glycosyltransferase;
SAP (serum amyloid protein);
C-reactive protein.
Panel 7: Anti-ischemic/Cytotropic/Lipid Peroxydation Panel
NADP/NADPH;
FAD/$FADH_2$;
intracellular $O_2$-radicals;
intracellular glutathione;
RBC-2,3 DPG;
whole blood viscosity;
plasma viscosity;
intracellular ADP.
Panel 8; Vascular Endothelial Cell Injury/Glomerular Injury/Vasodilatation Panel
AgPAI1;
1-0-hexadecyl PAF;
endothelin-I;
TNF-α;
IL-6;
IL-1;
whole blood viscosity;
plasma viscosity;
intracellular ADP.
Panel 9: Vascular Endothelial Cell Injury, Glomerular Tubular Injury, Microvascular Tone Panel (In addition to anti-inflammatory parameters)
AgPAI1;
1-0-hexadecyl PAF;
endothelin-I;
TNF-α;
IL-6;
IL-1α;
endothelial cell relaxing factor (EDRF);
6-keto-PGF1α,
γ-enolase (PB/lymphocytes) (cell differentiation marker);
creatinine;
creatinine clearance.
Panel 10: Autocrine Panel (Constitutive Transcription of IL-6, Mesangial Proliferative Glomerulonephritis, EBV induced)
Genomic Disease Panel (Lymphoma/Castleman's Disease (Translocation of c-myc Oncogene), Autoimmune Disease (Rheumatoid Arthritis), Chronic Fatigue Syndrome, HIV induced B-cell Differentiation, Atrial Myeloma)
IL-6;
protein Kinase A type II catalytic subunit;
protein Kinase A type II regulatory subunit;
1,2-diacylglycerol;
phosphatidyl inositol bi-phosphate;
inositol tri-phosphate;
intracellular $Ca^{2+}$;
protein Kinase C;
phospholipase C;
cGMP;
cGMP phosphodiesterase;
$PgE_2$;
$PgI_2$;
intracellular oxygen radicals.

One critical marker is chosen at each respective stage of the repair process and the maximum efficacious dose for that marker established. Administration of that dose induces correction of other stage-specific markers not necessarily identified or aimed at during therapy (i.e., "stage specific pleiotropism"). Following normalization of the first chosen marker, a second marker which continues to deviate from the normal condition is chosen. The dose that normalizes the second marker (i.e., the higher dose) is likely to further improve the first marker incrementally.

Initial administration of the selected dosage is followed by incrementally increasing dosages until the "maximum efficacious dose" is reached. A panel of laboratory assays to determine the state of the markers (e.g., absence, increase, decrease) is repeated every 3 to 7 days during therapy. These results together with the clinical markers of disease would indicate whether the defibrotide, or other nucleic acid derivative, is adequate in dose and duration to cause improvement in the pertinent marker or markers while simultaneously being totally safe to administer. Therapy is continued with escalating doses over sufficient time to assure complete normalization (i.e., the clinical laboratory assays, when compared to the reference range, are indicative of the normal condition) of the pertinent markers. When normalization is reached, therapy is stopped.

Although therapy is discontinued, the patient is tested weekly for the current state of the pertinent disease marker. If relapse occurs, therapy is reinitiated at the highest dose level of the prior course of therapy until normalization is again reached. While optional, it is advisable to continue escalating the dose level to potentially reach a shorter duration of therapy.

The highest tolerable dose per day which is complication free (e.g., no bleeding, thrombopathy) is preferred since treatment periods are usually shorter at higher dose levels. Therapy cycles are repeated until there is complete and irreversible normalization of the pertinent markers at which point the patient is cured. A marker is considered to be irreversibly normalized if it remains normal for three months without therapy.

There is a certain dose level which will ultimately give plateau levels on a particular marker, and irrespective of how long the dose range is continued, the level of the molecule will not go higher unless the dose (or cellular uptake of the respective nucleotide) is increased. This agrees with accepted biochemical knowledge, i.e., the more the number of receptors receiving signals, the more cAMP is produced and, as a consequence, the higher the transcriptional activity pertaining to vWAg is.

Minimum effective dosing is therefore counterproductive and markers have to be used to assess the maximum efficacious dose. Application of the higher dose will promptly lead to higher levels in a shorter time (high m-efficiency score).

This is confirmed from the cellular uptake curves.

Once a plateau is reached with the maximum efficacious dose, the m-efficiency score can thereafter be used along with the maximum highest levels of the last day to assess how long therapy should be continued to complete the repair process, i.e., when the maximum efficacious dose is continued when m-efficiency score is less than 1.0, the nucleotide no longer exerts any further therapeutic effect. This observation leads to the statistical definition of "maximum therapeutic dose," i.e., the time slot of the total administered dose beyond which further repair of the selected marker would not take place at that particular dose level.

While one skilled in the art, based on the information presented herein, would be able to detect and determine finer disease/repair markers so as not to miss complete cure, a standard panel of markers are given above which markers can be routinely repeated in each patient. Any abnormality in any marker should prompt reinitiation of therapy, even if no visible disease markers are observed, since many of the markers of the subclinical stage will be biochemical molecules, such as endothelin-I.

Treatment in Accordance with the Invention

A preferred embodiment of the treatment method applicable to all disease states treated according to this invention is diagramed in FIG. 1. An initial laboratory test panel (box 1) is first run which would consist of the respective set of "disease markers" and the universal panel of "repair markers" consisting of signal transduction/second messenger panel molecules. Additionally certain laboratory assays are used to assure that the dosages are safe for the patient being treated. For defibrotide these may include prothrombin time, activated partial prothromboplastin time, thrombin time, reptilase time, bleeding time, platelet function assays and coagulation factors (see baseline coagulation panel). "Disease markers" are utilized to indicate the overall therapeutic efficacy of the doses. These markers may be identified through blood tests, urine tests, clinical observation or identification of blood clots by any of several conventional techniques, or by the more refined techniques such as DNA fingerprinting and PCR. To evaluate the "disease markers" the laboratory analyses measure levels of certain proteins, lymphokines, enzymes and relevant molecules. Clinical markers may include blood pressure, visible tissue damage, signs of inflammation, ecchymoses, and the like.

An initial bolus of defibrotide (box 2) is given intravenously over 15 to 30 minutes. Immediately thereafter the patient is given the daily dose of 40–400 mg/kg by continuous infusion. Preferably, the initial dose is a bolus (25–50 mg/kg) followed by 24-hour dose which is increased in 50 mg/kg/day increments every 1–3 days. The starting baseline dose may be from 40–400 mg/kg/day depending upon physician preference and the respective disease state treated. Lower initial doses are preferred for those therapeutic compounds which enter the cell nucleus more readily and are thus effective at lower doses. The bolus and daily dose for chemical derivatives of the nucleic acids may be calculated as a proportion of the defibrotide dose based on the relative cell-entry rate. It is preferred to administer this dose intravenously using two IV bags of 50 ml D5W, each bag infused over 12 hours. If for any reason the infusion is interrupted, the rate of infusion would be thereafter adjusted so that the patient will have received the calculated 12 hour dosage at the completion of the specified time period. This 24 hour dose range can also be administered in 2–4 bolus injections or per oral administration.

Defibrotide or other selected nucleic acid derivative may be administered parenterally or orally. Parenteral administration is in the form of continuous intravenous infusion or intravenous bolus injection. Intravenous infusion may be accomplished by gravity feed, pump delivery or other clinically accepted methods. Oral administration may include the use of capsules, tablets or powders for any method of enteric administration.

To permit clinically practicable administration of defibrotide in the amount necessary, materials for delivery of the agent optionally comprise 2×50 ml D5W IV bags each containing one-half of the calculated total 24 hour dose in milligrams of defibrotide, each bag infused over 12 hours for the IV-continuous infusion at the maximum tolerable doses. Alternatively, the total 24-hour dose can be administered by bolus injection every 8–12 hours. The initial bolus injection and the subsequent outpatient bolus maintenance infusions are given, for example, in 3×25 ml D5W bags, each bolus to be infused over fifteen to thirty minutes. The oral dosage outpatient maintenance therapy in milligrams given daily (divided into 3–6 doses by mouth) would be the multiples of 2× the maximum tolerable IV dose.

The same dose is given for three days and the laboratory test panel is repeated (box 3). A full coagulation profile and tests for markers should be run before and after any dose escalation. These tests results are compared with the initial test data to determine if any of the markers (which may include laboratory data or clinical observation for the disease being treated) have changed. A change is expected to occur in at least one marker within 3–21 days, indicating that defibrotide is having an effect. After each test the dose of defibrotide is increased by 50 mg/kg/day, dose for chemical derivatives being proportional to the cell entry rate for the respective nucleic acid, and continued at that dose for three days before retesting. This pattern of escalating the dose and repeating the laboratory panels is repeated (boxes 4 and 5) until the patient's "maximum tolerable dose" (MTD) is reached or until the disease/repair markers have plateaued or completely normalized.

As evidenced by in vivo studies, it has been discovered that defibrotide, when administered to humans, decreases AgPAI1 (plasminogen activator inhibitor antigen) production and increases AgTPA production most efficiently starting at a dose range of 40–80 mg/kg/day, optimum effects being reached at 300–400 mg/kg/day dose range and above.

It has also been discovered that defibrotide can be used as an alternate to, or as an adjunctive thrombolytic agent with t-PA, t-PA analogues, urokinases, streptolinases and their derivatives, when used in dose ranges of 300 mg/kg/day or above in the treatment of venous thrombosis and arterial thrombosis. In addition to being an adjunctive antithrombotic agent, defibrotide is also an effective adjunctive antiplatelet and cytotropic agent to t-PA, t-PA analogues, urokinases, streptokinases and their derivatives.

Defibrotide is the drug of choice over aspirin as an adjunctive therapeutic agent to thrombolytic therapy at dose ranges starting at 40–80 mg/kg/day, most preferably 200 mg/kg/day and above. Defibrotide can also be used with vasopressin as an adjunctive therapeutic agent in thrombolytic therapy at dose ranges starting with 40–80 mg/kg/day, preferably 300–400 mg/kg/day or above. It is also the drug of choice over prostaglandins as agents that elevate cAMP levels to be used, as either adjunctive agents to thrombolytic therapy or antithrombotic therapy, or alone at dose ranges starting with 40–80 mg/kg/day, with optimum effects being obtained at 200 mg/kg/day and above. It is, likewise, the drug of choice, either alone or as an adjunctive, to agents that elevate cGMP at dose ranges starting with 40–80 mg/kg/day with optimum effects being obtained at 200 mg/kg/day and above.

In diseases involving vascular endothelial cell, dose escalation should continue preferably until vWAg is greater than five times the initial baseline level. The upper limit may vary among the various derivative nucleic acids depending on their respective cell entry rates. For the prototype nucleotide, i.e., low molecular weight defibrotide, the safe upper limit is at least about 400 mg/kg/day and may reach 600 mg/kg/day. For the high molecular weight (45–50 kDA) defibrotide the sale upper limit is about 350 mg/kg/day. The dose ranges with the chemical derivatives of the nucleotide would correspond to dose ranges that elevate the base line vWAg antigen level to 5 times the initial value.

If three consecutive values for a selected marker are about the same, a plateau has been reached. This procedure is followed for a minimum of 21 days (box 6). Disease/repair markers are checked and coagulation profiles are run on weekly intervals to monitor response. If no response is observed, i.e. no change in the level of any marker (box 7), therapy is discontinued (box 8), and treatment is determined to have failed. If, after 21 days (box 6), no plateau is reached, but improvement in the disease markers has occurred (box 14), the dose may be doubled or the MTD may be given (box 15).

If the markers are normal (box 9), therapy is discontinued (box 10). Tests continue to be repeated weekly for up to three months, noting any change in markers that would indicate relapse. If no relapse has occurred and no new markers have appeared after three months (box 11), therapy is discontinued (box 12) and the patient is considered cured. Should an old marker reappear or a new marker appear (box 13), the last previous dose is doubled, and therapy is resumed at that dose level. If doubling of the dose would exceed the MTD, the MTD would be administered.

Selection of Markers

The correct identification of markers are based on the identification of the pathways of disease pathogenesis and the respective repair processes and pathways. The mechanism of efficacy of the therapeutic nucleic acid simulate or are superimposed on the cellular pathways of the respective repair process they induce. For example, using defibrotide as the clinical agent, one would (1) identify the known signal transduction systems and second messengers of the repair process, (2) define the most probable nucleic acid-induced repair markers of the known cellular repair pathway, and (3) define markers of the disease process related to disease pathogenesis.

Many disease processes are pathogenically based on overactive body defense mechanisms. As such, a compound whose intracellular concentration can be a repair marker in one disease state can be a disease marker in another disease state. In such a case, the marker would usually be under-regulated by defibrotide instead of induced. Similarly, a marker of normal cellular function, if deficient, may be a disease marker. For example, the paralysis of cellular function of CD4 cells by the HIV retrovirus is secondary to the compromise of normal cellular markers of transduction pathways and second messengers.

G-proteins instrumental in the activation of adenylyl cyclase are likely to be deficient in their active form with a low dose threshold level. In this case, the deficiency of the normal cellular marker of G-proteins would be a disease marker. Since defibrotide affects the adenylate cyclase pathway (increased cAMP by defibrotide), defibrotide would restore the second messenger of cAMP, which therefore would be a repair marker.

Several disease specific markers may be present in patients in need of treatment. For renal failure, disease specific markers include blood pressure, creatinine clearance, creatinine, fPAI, and fPAI/AgTPA. For prothrombotic states and thrombotic diseases, disease specific markers include protein CA, protein CI, protein SI, F-IX, F-XI and F-XII and APTT. For established thrombotic states, specific disease markers include fPAI/AgTPA, protein CA, protein CI and protein SI whenever there are no concurrent changes in F-IX, F-XI and F-XII. For acquired thrombopathy disease markers include bleeding time and platelet aggregation with arachidonic acid and other platelet aggregation assays. For HIV disease markers include arthralgia, Herpes labialis, Herpes genitalis, and cryptococcal diarrhea.

When considered in conjunction with the published literature, the data reported herein demonstrates that defibrotide acts upon endothelial cells to revive an inadequate functional state of the normal cell. The first successful in vivo human pharmacological experiences of the effects of defibrotide on the inhibition of lipo-peroxidation and reversal of cyclooxygenase inhibition by the administration of correct dose level are shown herein.

In addition to playing a role in the diseases discussed above, endothelial cells play a prominent role in heart disease, liver disease and kidney disease. Defibrotide has cyto-protective effects in myocardial cells and hepatic cells, as verified in patients with tissue necrosis; marker dependent doses of defibrotide can effectively treat these diseases. For heart disease, protein CA, protein CI and protein SI will be additional, yet optional, disease markers. Disease specific markers for liver diseases include SGOT, SGPT and GGPIT. Disease specific markers for kidney disease include creatinine, creatinine clearance, blood pressure, 24-hour urine volume, and 24-hour urine protein. vWAg and platelet aggregation by arachidonic acid will also be markers for these diseases.

To increase second messenger markers of the above pathways, the maximum efficacious dose is the dose which will normalize the platelet aggregation assays, so as to established normal levels of 60–150% in all cases. Defibrotide and derivative nucleic acids are the first side-effect free platelet deaggregatory agents which induce this effect by restoring the integrity of the platelet functions (which by definition inhibit aggregation), and not by creating further defects in platelet functions like, for example, aspirin would. Hence this study shows the therapeutic nucleic acid to be the first proplatelet agent to be used within the arena of anti-platelet therapy.

The maximum therapeutic dose in turn would again follow the guidelines described above for vWAg, since this universal marker will get elevated with modulation of any phase of repair process such as, for example, receptor up-regulation, signal transduction or induction of translation and/or transcription, shutting off of transcription/translation which in turn may happen by activation of CREM, which is the inhibitor transcription factor of CREB, i.e., the latter is cAMP dependent initiator of the transcription of factor of the CRE which in turn is the portion of the DNA enhancer sequence responsive to cAMP and cAMP associated transcription factors, such as c-myc products, c-fos products, ATP Activation Factor, Serum Responsive Element (SRE), API transcription factor (ATF), HIV-Long Terminal Repeat (LTR), leucine zipper transcription factors of c-fos/c-jun. (ATF, SRE, API sites in c-fos promoter/enhancer all respond to cAMP without the requirement of SRE. Protein Kinase A activates endogenous CREB activity and will enhance viral transactivation).

During therapy increasing prototype markers of protein CA, protein CI and protein SI are representative markers for both transcriptional and redox state effects of this class of nucleotides. Along with platelet aggregation markers, they represent pharmacologically the antithrombotic actions of the nucleotide and its derivatives at the respective dose levels. These representative dose levels for the antithrombotic effect of this nucleotide is ideally to start at 120 mg/kg/day dose level or above. The projected dose values show, unlike the purely transcriptionally activated molecules like AgTPA and vWAg, progressive potentiation of the antithrombotic effects of the nucleotide without any slowing down or leveling off at higher dose levels. This is in keeping with the fact that besides modulation of the redox state and transcriptional/transitional modulation of the respective molecules, antithrombotic action also depends on the "heparin-like" activity of the nucleotide measured in the laboratory with anti-factor Xa activity, PT/APTT, thrombin time, reptilase time markers. Hence the prototype nucleotide and derivatives proposed are alternative pharmaceutical agents with dose ranges starting with 120 milligrams per kilogram per day.

The studies reported herein support applicant's discovery that native defibrotide and chemical derivatives thereof are the pharmaceutical agents of choice in all the thrombotic disease states associated with the presence of a lupus anti-coagulant and other anti-phospholipid antibodies. Since elevation of the protein CA levels also involves activation of vitamin K via modulation of the redox state, the same levels are representative also for the nucleotide's actions at those levels involving lipid peroxidation, oxygen radical-induced injury states associated with impaired perfusion of organs or hypoxemia. Disease states involving the modulation of the anti-phospholipid antibodies include clinical states such as myocardial infarction, valvular cardiac lesions, glomerular tubular renal lesions, leak proteinuria, nephrotic syndrome, skin and soft tissue necrosis, deep vein thrombosis, and post phlebitic syndrome related to the presence of lupus anti-coagulant and anti-phospholipid antibodies. The nucleic acid also induced complete disappearance of the circulating anti-phospholipid antibody for the duration of drug administration. Although the clinical beneficial effects were irreversibly established after cessation of drug administration, circulating anti-phospholipid antibody levels returned to abnormal values, albeit without any clinical abnormalities accompanying reappearance of circulating antibodies.

Endothelin-I is constitutively released from the vascular and the endothelial cell, secretion of endothelin-I being regulated at the transcriptional/transitional level. Gene expression of endothelin-I depends on protein kinase C pathway which has been shown in this study to be suppressed by the prototype nucleotide, i.e., high molecular weight defibrotide. Hence, the dose level that suppress transcriptional/transitional activity involving protein kinase C pathway is also representative of the dose level at which the prototype nucleotide will be able to suppress or inhibit the protein kinase C pathway; including the receptor-ligand interaction, inhibition of inositol triphosphate and diacylglycerol and inhibition of release of $Ca^{2+}$ intracellular levels. Action by this nucleotide has been qualitatively mentioned and shown in the prior art. However, doses representing the corresponding protein kinase C pathway inhibition have not been outlined in humans until this study. High molecular weight defibrotide will suppress endothelin-I levels starting at dose levels of 40–80 milligrams per kdlograms per day ideally at dose ranges of 160–200 milligram per kilogram per day or above. Dose levels of 275 mg/kg/day depress interleukin levels. High molecular weight defibrotide will furthermore balance activation of phosphoinositol/diacylglycerol signal transduction pathway also at the same dose levels.

Preservation of β-adrenergic receptor functions and prevention of α-adrenergic receptor overactivity by defibrotide has been described qualitatively in prior art animal models. However, human treatment doses starting at levels of 80–120 milligrams per kilogram per day, optimally seen at 160–200 milligrams per kilogram per day and above, have for the first time been used to treat humans. These doses have been deduced from the dose ranges arrived at via platelet aggregation studies.

Intact polymorphonuclear leukocytes (PMN) are the most efficient circulating blood cells that convert $PgI_2$ or 6-keto-$PgI\alpha$ into 6-keto $PgE_1$ by activation of 9-keto reductase. This conversion requires the presence of injured endothelial cells suggesting that endothelial cells activate 9-keto reductase to generate 6-keto $PgE_1$ synthesis, involving cell-to-cell interaction. $PgE_1$ plays a much more important role in regulating the antithrombotic activities of platelets in response to injury, this effect being much more pronounced than the one exerted by $PgI_2$.

PMN metabolize linoleic acid into 13-HODE under basal conditions. Down regulation of platelet adhesion to endothelial cells following vascular wall injury in vivo was in part due to the presence of 13-HODE in PMN at the site of injury. Prior art has shown in the annular flow chamber that adhesion of platelet to the thrombogenic surface was inversely correlated with PMN 13-HODE levels. However, no therapeutic agent increasing $PgE_1$ generation and 13-HODE generation has heretofore been identified.

Injury-dependent increases in the $PgE_1$ and 13-HODE molecules, requiring endothelial cell lesion are mirrored by defibrotide induced up-regulation of adenosine $A_1$ and $A_2$ receptors—which up-regulation is also an injury dependent event. Up-regulation of adenosine Al and $A_2$ receptors are inductive to generation of prostanoids, namely $PgI_2$ which is converted into $PgE_1$ by the injured endothelial cell. The present study has identified the only pharmaceutical agent thus far, namely defibrotide and derivatives thereof, that increase $PgE_1$ generation as well as provision of 13-HODE, which are shown in the prior art to be the most important antithrombotic and platelet deaggregation molecules secreted by PMN. This is also in keeping with the showing that defibrotide will induce deaggregation of platelets as well as decrease the PMN numbers in the septic shock animal model. The pertinent markers for proplatelet effect are: intracellular $Ca^{2+}$, intracellular cAMP, platelet factor 4, platelet β-TG, glycoprotein 1b, collagen/arachidonic acid stimulated ATP secretion by platelets, platelet activating factor (PAF), 6keto $PgE_1$ ($PgI_2$ metabolite in plasma), 6-keto $PgI_{1\alpha}$ ($PgI_2$ metabolite in plasma), 13-HODE (PMN), 5-HETE (PMN), 6 PgE 1/5 HETE ratio. (Intracellular calcium level is routinely measured by Quin-2 method). NADPH oxidase exists in some membranes of inflammatory phagocytes. Prior art has shown increased NADP ratio with the prototype nucleotide defibrotide.

Markers AgPAI1 and endothelin-I are representative of existing endothelial cell injury involving the vascular endothelial cell glomerular basal membrane and nephrogenic microvascular vascular spasm. Hence, markers for endothelial cell injury are AgPAI1, endothelin-I, TNF-α, IL-6 and IL-1.

The prototype high molecular weight defibrotide, native defibrotide, low molecular weight native defibrotide, and chemical defibrotide derivatives regulate genes which are regulated by cAMP. These genes include vasoactive intestinal peptide (VIP), somatostatin, human chorionic gonadotropin, phosphoenolpyruvate carboxylkinase, tyrosine hydroxylase, fibronectin, prolactin, ornithine decarboxylase, interleukin-6 gene, c-fos oncogene, haptoglobin, hemopexin, C-reactive protein (CRP), as well as other cellular genes which are regulated by cAMP responsive element (CRE), transcriptional factors interacting with CREB (which is 43 kd protein that interacts with CRE via leucine zipper, such as c-myc products, c-fos products, ATP (Activating Protein), SRE (serum responsive element), API. Protein kinase A will activate endogenous CREB activity and will also enhance viral transactivation. CRE/CREB related transcription of genes including HIV Long Terminal Repeat (LTR) will be positively induced with high cAMP levels.

The selected nucleic acid, e.g., defibrotide, will affect only injury-dependent parameters in each individual patient. As such, no uniform action will be observable in all patients. For the nucleotide transcriptionally-activated parameters, analysis is made for the highest values in each dose range. For the nucleotide transcriptionally shutoff parameters, analysis is made for the lowest value in each dose range.

Therapy Based on Universal Markers

Several prototype markers have now been shown to reflect transcriptional genomic activity by nucleotides which increase cAMP, adenylate cyclase via the interaction of G-proteins, and phosphorylate transcriptional factors via protein kinase A. These markers are vWAg, AgTPA and $β_2$-microglobulin. While vWAg and AgTPA are representative markers, any molecules which are initiated by nucleotides, or derivatives such as defibrotide, to induce transcriptional activity are included.

It has been discovered that vWAg may be employed as a universal marker to guide the assessment of the duration of therapy, i.e., the most therapeutic dose, as well as the most efficacious daily dose. It has been discovered, as reported herein, that vWAg is transcriptionally activated by defibrotide irrespective of the type of injury. Analysis of patient data has led to the unexpected finding that with the onset of cure, vWAg levels decline. The production of vWAg will be activated by defibrotide only for the duration of the injury and the repair process. In this regard, defibrotide will not effect vWAg levels in healthy individuals or following the establishment of cure, i.e., vWAg level will decline to baseline regardless of ongoing therapy. Concurrent analysis of vWAg with various "disease markers" correlated with changes in the disease marker levels. In other words, it has been discovered that therapy dependent absolute changes in disease markers (decline or increase) correlate with peak vWAg levels. The normalization of disease markers, in turn, correlates with decline in vWAg levels.

von Willebrandt antigen (vWAg) is classified according to this invention as being a universal dose marker. vWAg can be utilize as the universal marker for all nucleotides that induce activation of cAMP and protein kinase A enzymes. vWAg is a plasma glycoprotein having a molecular weight of approximately 200,000 which is constitutively secreted by the endothelial cell. It is important in hemostasis as a prothrombotic factor (factor VIII/vWAg protein) and as an inducer of adherence of platelets to the exposed subendothelium. In every disease state, vWAg levels go up with increasing defibrotide dose levels when the dose is adequate to stimulate vascular endothelial function.

In accordance with the invention, an increase in the vWAg level corresponds to the induction of transcriptional activity of this gene by the nucleic acid. Elevation of vWAg is representative of the ongoing repair process. The decline in the level and eventual normalization of vWAg during therapy is representative of the cure process. Plateau in the level of vWAg correlates with the application of the maximum efficacious dose. Without exception, the elevation in the level of vWAg is concurrent with modulation of the disease marker and activation of the repair marker. Here the maximum efficacious dose is determined along with vWAg, so as to normalize the levels of these molecules between 65–150%, and eliminate the intracellular oxygen radicals (measured by chemiluminescence, normal state being negative). For the prototype drug, defibrotide, the maximum efficacy in inducing transcriptional activation of vWAg occurs at doses of 40 DKGD and above, ideally within the DKGD range of 40–400. The universal marker vWAg dose levels are representative dose levels by the prototype's transcriptional/transitional modulatory effects. Fitting the definition of universal marker, vWAg does not contribute to the expected correction of bleeding time but acts as a functionally dormant molecule.

Another option is to empirically repeat therapy after three weeks following cessation of therapy on the above principles. In this regard, the half life of the nucleic acid appears to be about three weeks, based on the observation that the universal marker vWAg requires 2–3 weeks to come down to baseline levels with cessation of therapy. If the universal marker vWAg is elevated during therapy with the previous maximum efficacious dose, there is still a lesion to treat, irrespective of the fact that there are no known or visible clinical, and/or documented biochemical repair or disease markers.

Therapy, in accordance with the invention, is geared to continue until vWAg is normalized while on established maximum effective dose. Thereafter therapy is discontinued and the same cycles are repeated until the maximum efficacious dose therapeutically initiated no longer induces any elevation in vWAg, as would be observed in a normal healthy individual.

While platelet aggregation with arachidonic acid, ADP 20, ADP 10, ADP 5 and collagen also are therapy increasing markers, they are not representative markers for the transcriptional activity of the nucleotide. Rather, they constitute markers for the various receptors the corresponding statistics of which are to be interpreted as for vWAg and AgTPA. The dose ranges are representative of the dose ranges affecting receptor ligand interactions as well as stimulation of prostanoid secretion by the prototype nucleotide, since prior art has shown that defibrotide up-regulates Adenosine $A_1$ and Adenosine $A_2$ receptors (represented in this work by the up-regulation/normalization of the arachidonic acid and ADP induced platelet aggregations). Prior art also has shown that up-regulation of Adenosine $A_1$ and Adenosine $A_2$ receptors is inductive of up-regulation of $PgI_2$ secretion, independent of cyclooxygenase/arachidonic acid pathway. In this study for the prototype (defibrotide) up-regulation of Adenosine $A_1$ and $A_2$ receptors and cyclooxygenase pathway-independent secretion of prostanoids occur optimally at dose levels of 120–200 mg/kg/day, the effect starting at dose levels of 40–80 mg/kg/day. These constitute also the optimal dose levels for the "pro-platelet" effect of defibrotide. While projected dose-levels indicate beyond 400 mg/kg/day the added benefits may be negligible, these higher dose levels are to be considered for the low molecular weight native defibrotide. For the chemical derivatives with varying degrees of cell-entry the optimal dosages would be corresponding to dosages increasing vWAg levels to 5×the baseline.

Hence analogous to the induction of top transcriptional activity, induction of the optimum receptor/ligand interaction would also require that the vWAg level be raised 5 times (or 500%) and cAMP to 100% of the baseline levels, respectively, since 100% occupation of epinephrine/norepinephrine receptors (prototype receptor/ligand interaction for defibrotide and derivative nucleotides) would translate into 100% increase in intracellular levels of cAMP via activation of adenyl cyclase enzyme. To induce the cell at the top performance level in either shutting off or turning on of the repair molecules, the maximum efficacious dose has to be increased to reach these numerical values. In turn the maximum therapeutic dose is determined by when the vWAg and/or intracellular cAMP levels decline to baseline levels during therapy with maximum efficacious dose.

Even when the markers are normal and oxygen radicals are negative, the maximum therapeutic dose (until universal marker or vWAg returns to the baseline level during therapy) (established normal is 0.5–2.00 U/ml) is administered.

Markers representative of shutting off transcriptional activity by the nucleotide (or activation of the cAMP responsive CREB by CREM) are AgPAI1 and endothelin-I molecules. Here the interpretation has to be made in the opposite direction of induction of transcription/translation, i.e., maximum values of the lowest level (worst performance) on the last day should be followed to determine the maximum efficacious dose.

vWAg will increase whether the nucleotide is used for transcription induction, maintenance of the redox state, or modulation of second messengers of cAMP, directly or indirectly of opposing signal transduction pathways of intracellular $Ca^{2+}$, diacylglycerol and/or phosphoinositol, or with prostaglandin $PgI_2$ or $PgE_2$.

The maximum therapeutic dose with declining molecules will still be the duration and/or dose of therapy where vWAg becomes normal on therapy.

Maximum therapeutic dose will correspond to a m-efficiency value of less than 1.0, i.e., no further therapeutic effect. It will be understood that the levels do not decline into negative values, since such is not the normal state.

Statistical Analysis

A statistical model has been used to assess the dose and duration of therapy with the ultimate objective of irreversible cure. For each molecular marker, calculations are presented, based on analysis of the data from all treated patients, for the "first day value," the "last day value," the "highest value" or "lowest value" (i.e., for transcriptionally activated molecular markers and for transcriptionally inhibited molecular markers, respectively), the "m-efficiency score," and the "time required to reach the optimal effect of the nucleotide" at the dose ranges employed. It is noted that the "first day value" at a particular dose is the "last day value" of the preceding dose range. The "trend value" for each marker is calculated from examination of pooled actual patient data, i.e., the behavior of a particular marker in a particular dose range over the population. The projected values have been calculated and presented as "straight line variation," "logarithmic line variation" and "potential line variation," stratified into dose ranges with 40 mg/kg/day increments. The "minimum of increasing values" has been found to be the best parameter to follow for transcriptionally turned on molecules while the "maximum of the lowest values" has been found to be the best parameter to follow for transcriptionally turned off molecules.

The best parameter to follow the dose related induction of transcriptional activity is the "minimum values of the increasing levels" obtained on the first day of the initiation of each dose range. "Highest or increasing levels" represent the increase in level of a molecule whose production (transcription) is turned on with increasing dose levels. Choosing the minimum increase in the level in the transcribed genome among all patients treated in any dose range enables the prediction of the worst performance with that dose of the therapeutic compound. This enables the treatment of the worst performer, which allows turning on the genomic transcriptional activity in the greatest number of patients within each respective dose range. Increase in the marker, as shown by "minimum highest value" represents that the repair process is ongoing, that is, repair molecules are being produced and transcriptional activity is ongoing.

The quantitative relationship between vWAg level and daily dose of the therapeutic compound is best visualized when the minimum value of the increasing vWAg levels in the population are analyzed (i.e., the worst performance levels in any one patient at any one dose range, "worst performance" implying that increasing the dose will incrementally continue to elevate the vWAg, which is biologically interpreted as meaning that there are more repair events to go through.

Minimum increasing value is the parameter to use to confirm the event of ongoing cellular repair. Maximum increasing value is the statistical parameter to use to follow the completion of the repair event. Maximum therapeutic dose is the dose at which vWAg on continued therapy will decline to a normal level.

As shown by the data presented herein, the "maximum values of the lowest levels" obtained among all patient data on the last days of treatment at each dose range are similarly used to analyze how increasing dose ranges affect the transcriptional activities involving the "turned on" molecules. The levels will show progressive declines, i.e., the progressive turning off of the repair process with the onset of cure, in spite of the higher doses.

Once maximum stimulation takes place (as assessed by the use of first day minimum highest levels), the cell gets turned off. By the use of the maximum lowest levels of the last day, therapy is continued at that particular dose level until these levels return to the baseline levels on therapy, i.e., until there is no more ongoing transcriptional activity, i.e., the repair process is completed.

The m-efficiency value is the ratio of the respective elevated level over the time taken for elevation to occur. The higher the dose, the higher the value of the numerator and the higher the m-efficiency level. Alternatively, the shorter the time (denominator), the higher is the n-efficiency value.

Method of Treating HIV-Infected Patients with Defibrotide

It has now been discovered that the administration of non-sequence specific DNA, such as defibrotide decreases Il-1, Il-2, TNF-α and Il-6, all of which are known inducer of HIV proliferation. Administration of such an agent also increases total lymphocyte and T-lymphocyte counts, CD4 counts, and CD8 counts, as well as increasing cGMP/cAMP ratios. An anabolic effect has also been observed.

Defibrotide's mechanism of efficacy relates to modulation of cell functions at the nuclear genomic level through one or more pathways by modulation of the cell's genetic material, i.e., DNA itself or translation or transcription of the genetic information. Defibrotide-induced cellular modulation restores the normal functions of the cell such as the production of normal proteins needed by the cell and, in the case of HIV, the correction of the effects of the abnormal, viral encoded genetic material by inhibiting its further production at the expense of the normal, virus-free genetic material. In the course of the multiphase treatment, defibrotide is administered at dosages much greater than previously described in the literature. Preferably, in treating HIV, an initial bolus dose of 100 mg/kg in 50 ml DSW is infused over a period of 30–60 minutes followed by 200 mg/kg/day infused in 250–500 ml DSW over a period of 3–24 hours. From day 2, dose is escalated to maximum tolerable dose, maximum efficacious dose and maximum therapeutic dose levels. The dosages and durations of the phases of therapy are adjusted according to the results of laboratory studies performed on the patient's infected cells. In this way, the HIV virus may be inactivated and its proliferation arrested. Therefore, the progress of the disease may be arrested or ameliorated.

Because HIV virus adversely affects the genetic material and function of the cells, defibrotide can effectively treat HIV infection as long as the carrier $CD4^+$ cell and/or the monocyte harboring the virus preserves the physiological ability to revive itself. Therapeutic success with defibrotide, however, is strictly dependent upon the assessment of the correct treatment doses for the respective disease states. Moreover, since the optimum function of the normal cell, by definition, would not be compatible with any complications, defibrotide at any defined maximum efficacious dose, specific for any patient and disease state would be complication-free.

Sarin et al. (*Proc. Natl. Acad. Sci. U.S.A.*, 1988, 85:7448–7451), as well as Leonetti et at. (*Bioconjugate Chem.*, 1990, 1:149–153), have shown that anti-sense oligonucleotides are potent inhibitors of HIV-1 replication in cell culture. The methylphosphonate linked oligonucleotides were found to be superior in this effect over the phosphodiester linked oligonucleotides, apparently as a result of their resistance to nucleases. This property was deemed to be the factor in the superiority, since oligonucleotides less than 20 bases in length proved to be ineffective inhibitors.

Efficacy of defibrotide may have several concurrently active mechanisms. Defibrotide may provide anti-sense neutralization of the viral proteins. Defibrotide's mechanism of efficacy may be at the nuclear level by modulation of genetic functions via other pathways as well. Defibrotide's actions may be more apparent during viral phases which involve translation and/or transcription of the DNA message, so as to revive the normal function of the cell at the expense of the disease-specific molecules. This action may be analogous to anti-viral effects of Ampligen (a mismatched double stranded RNA-molecule. However, whereas Ampligen exhibits immunostimulating effects, agents such as defibrotide are both immunostimulants and immunosuppressants. Defibrotide may modulate viral penetration into the cell via its known action of inhibiting intracellular calcium mobilization. Also, defibrotide may directly inhibit viral enzyme reverse transcriptase via inducing ATP production analogous to ddl (dedeoxyinosine), by virtue of its known action of inducing high energy metabolites (ATP, ADP, NADP/NADPH), possibly via modulation of Complex-I respiratory molecule. Defibrotide may inhibit protein kinase C analogous to Hypericin. Additionally, defibrotide decreases Tissue Necrosis Factor (TNF), a cytokine known to promote HIV-I activation, by its known effect on increasing cAMP levels at the correct defibrotide dose level.

Whatever the mechanism, zinc is known to have an inhibitory effect upon nucleases acting on phosphodiester linkages, as well as an enhancing effect on base pairing. U.S. Pat. No. 3,770,720, teaches that in the production of defibrotide, zinc should be removed from the molecule. However, in the treatment of AIDS, it is preferred that zinc be present. Moreover, it is preferred that iodine should also be present. In the defibrotide used in the Examples iodine was present in an approximate ratio of one zinc atom per iodine atom and a two to one ratio of zinc+iodine to nucleotide base.

Figure 2:
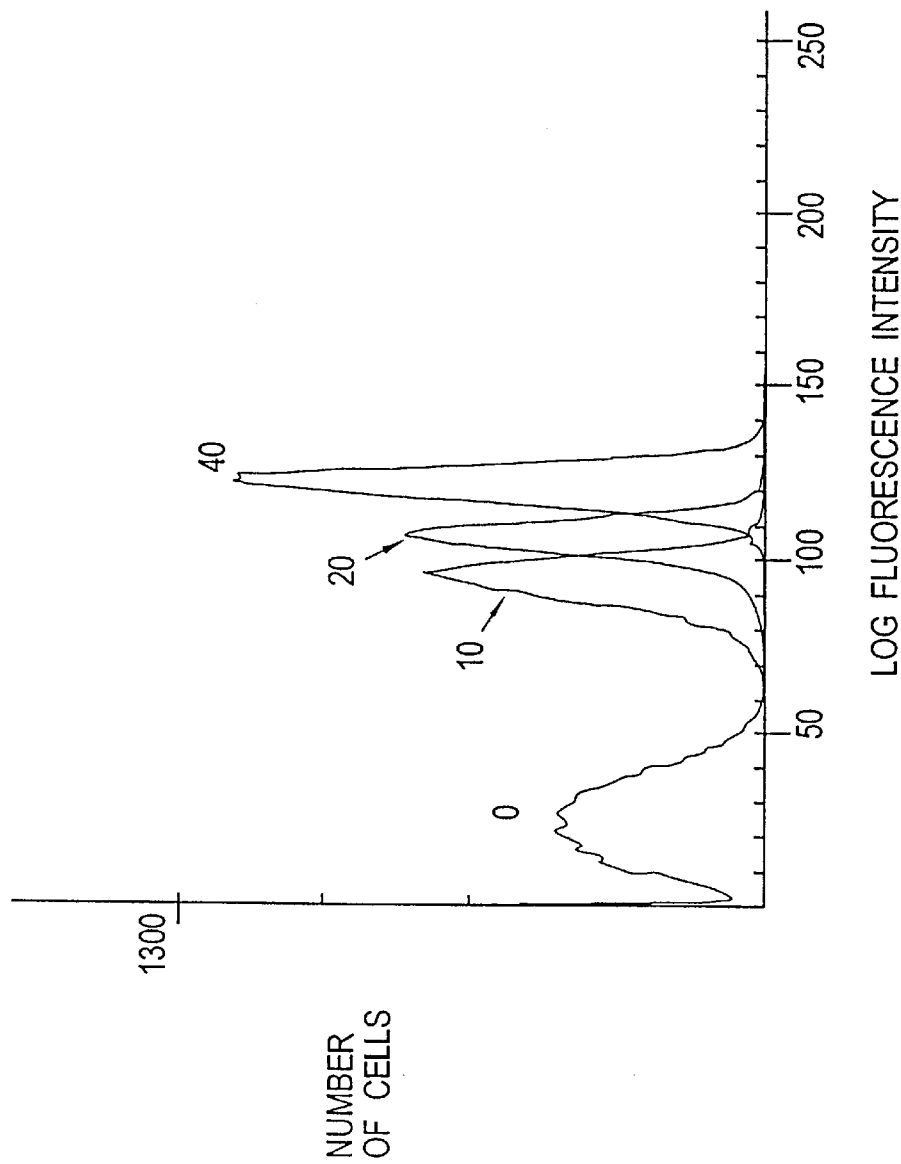
FIG. 2 is a graph showing normal peripheral blood cells labelled with 0, 10, 20 and 40 μg defibrotide-biotin combination.
Figure 3:
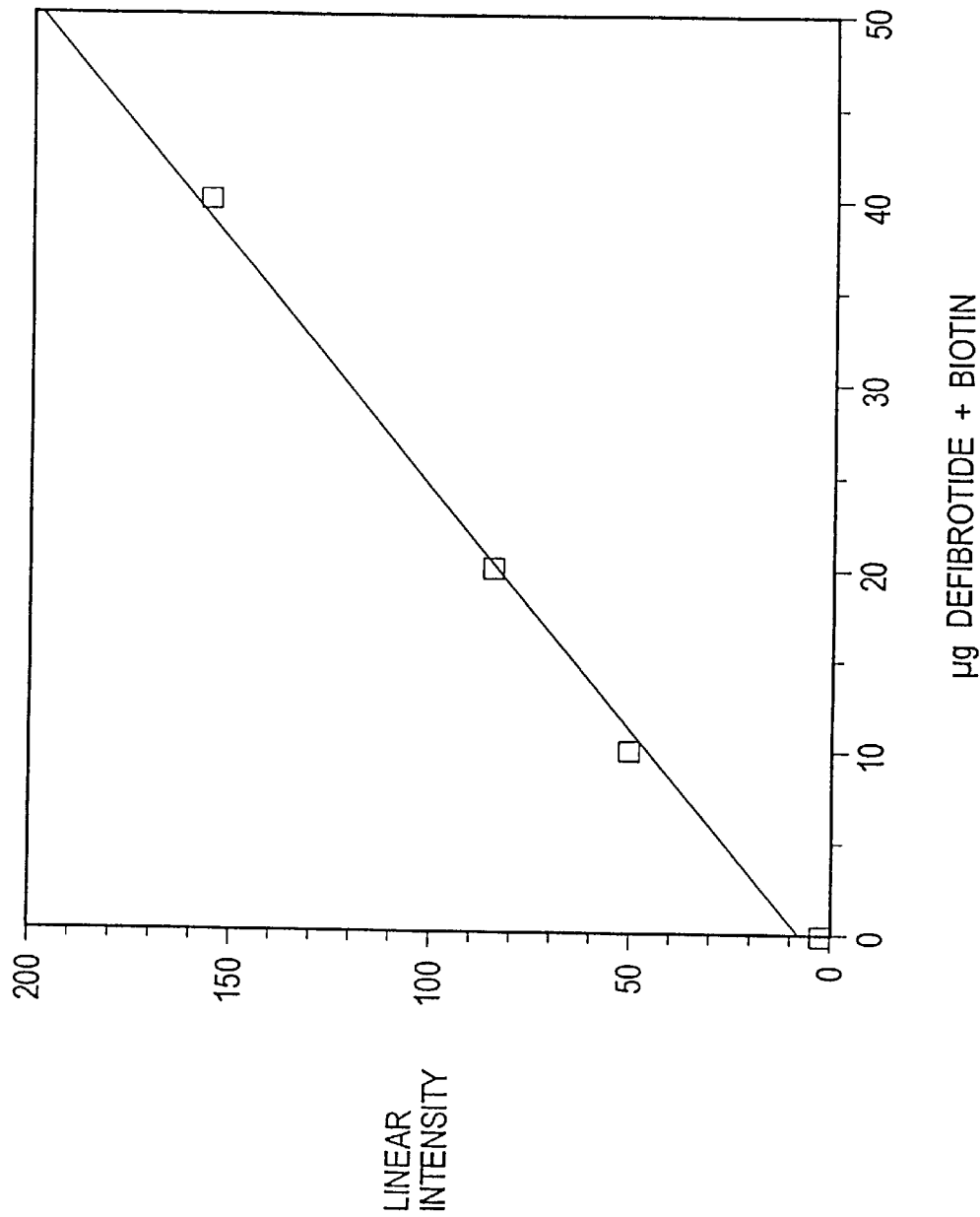
FIG. 3 shows the data of FIG. 18 on a linear scale.
Figure 4:
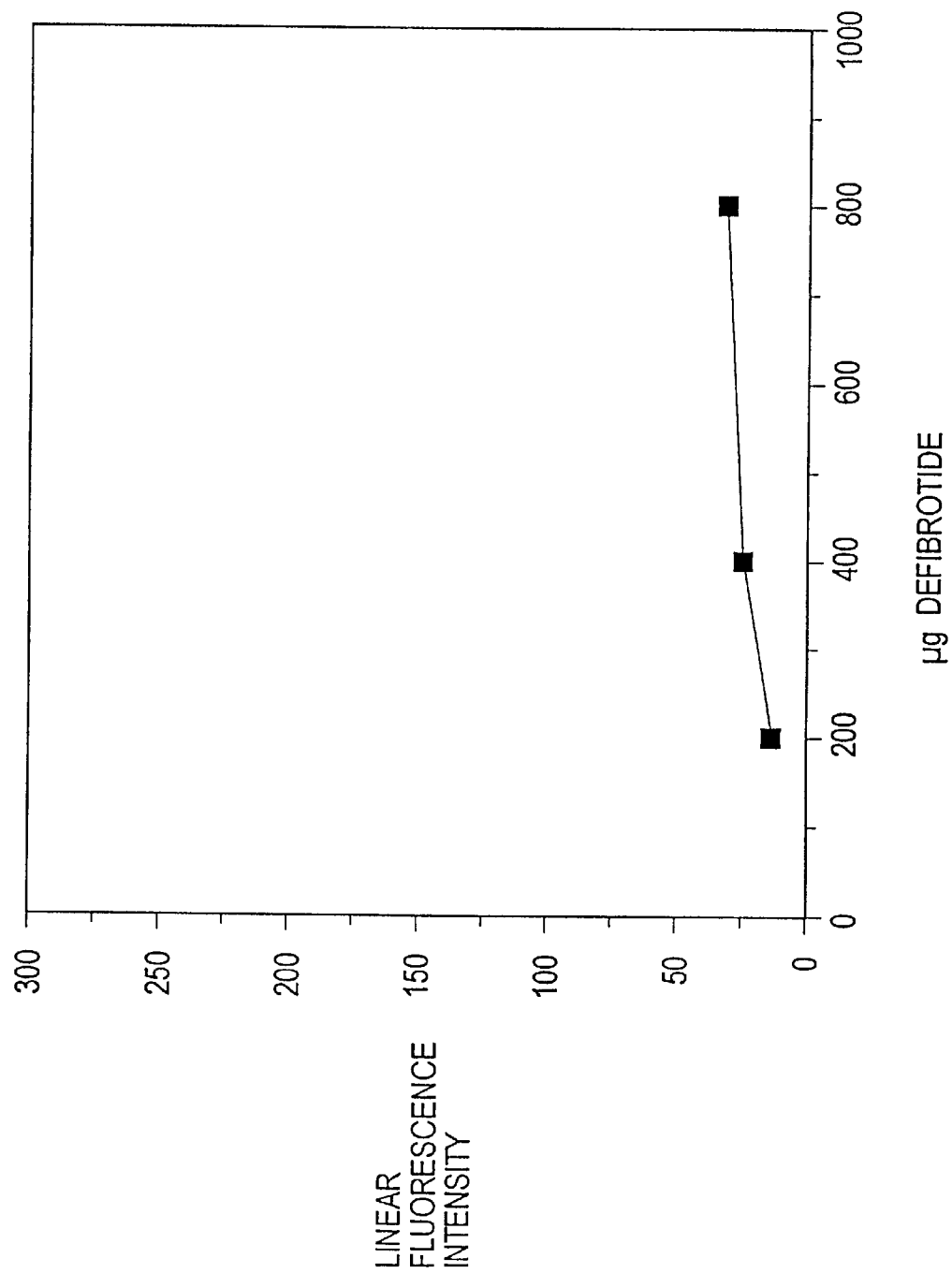
FIG. 4 is a graph showing the lymphocyte uptake of defibrotide without biotin and labelled with Cy5.18.
Figure 5:
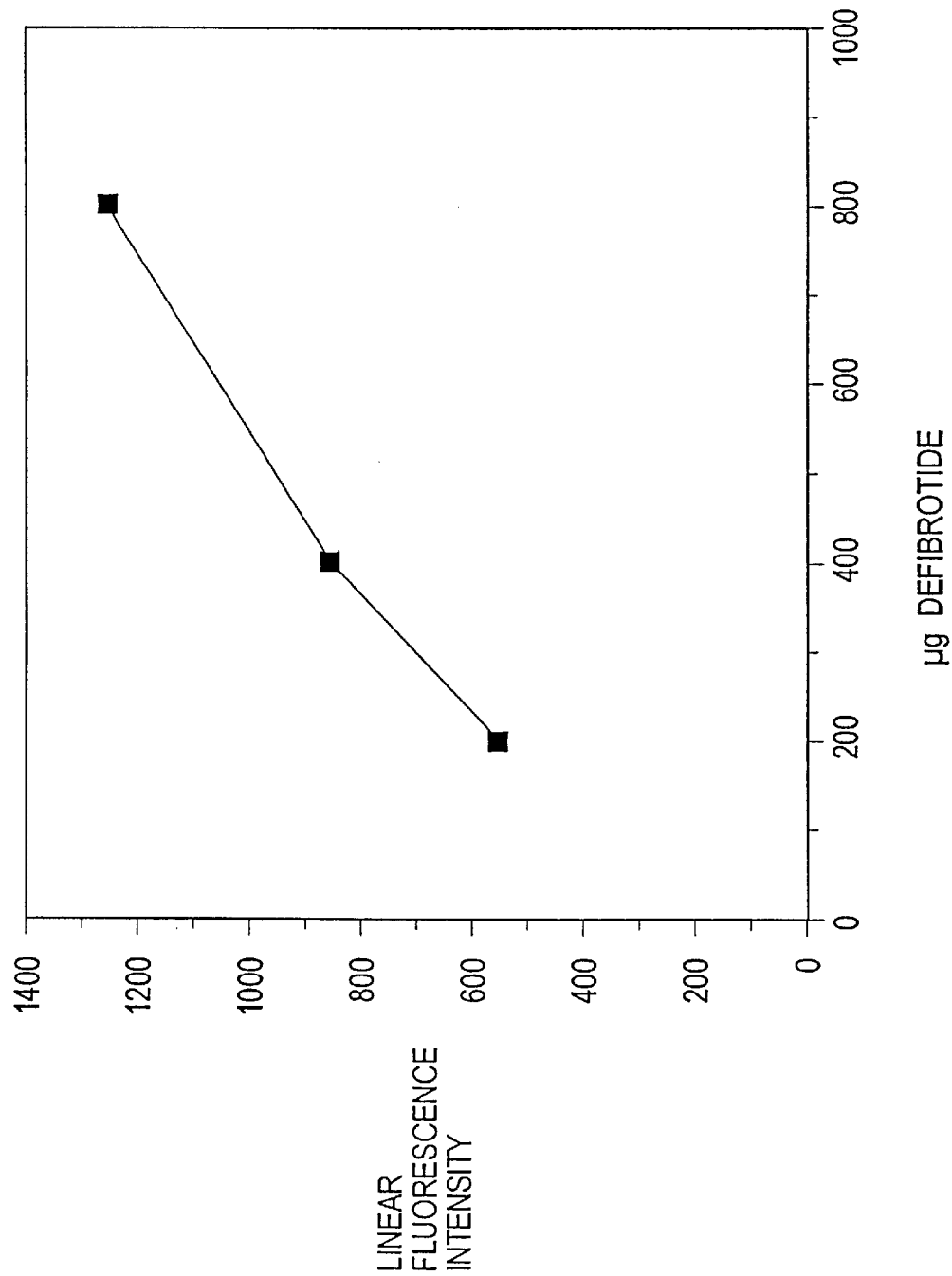
FIG. 5 is a graph showing the monocyte uptake of defibrotide without biotin and labelled with Cy5.18.
Figure 6:
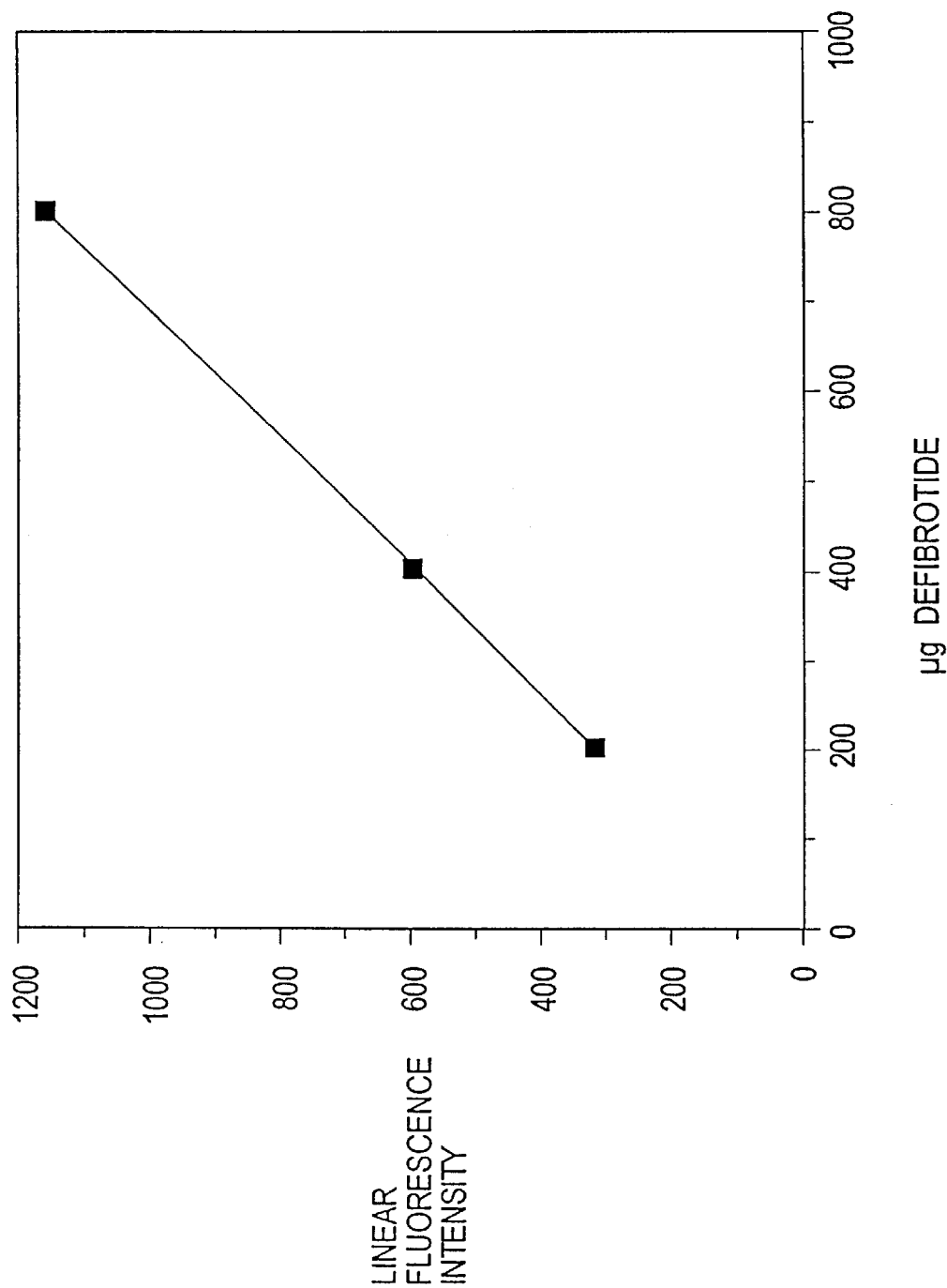
FIG. 6 is a graph showing the granulocyte uptake of defibrotide without biotin and labelled with Cy5.18.

As can be seen from comparing the cellular uptake data shown in FIGS. 2 and 3 with the data shown in FIGS. 4, 5 and 6, a greater level of defibrotide enters the lymphocytes when biotin is present. Horn et al. (*Plant Physiol,* 1990, 93:1492–1496) has observed that biotinylated molecules enter the cell via the folate endocytic pathway. The data of FIGS. 2–6 read in conjunction with the above-cited Horn reference, indicate that defibrotide with biotin may also use the folate endocytic pathway.

Defibrotide may jointly and/or selectively modulate one or several pathways. This modulation will be, only to the appropriate degree thus surpassing all of the other anti-HIV agents in its lack of side effects, yet presence of proven efficacy. Defibrotide will achieve this result only when the dose levels are tailored to the patient, stage of disease activity and/or reigning stage of viral activity.

AIDS virus can manifest itself in four basic stages which are well known in the art and described in the medical literature: 1) HIV positive blood test but otherwise no abnormal laboratory findings or clinical symptoms; 2) pre-AIDS Related Complex (pre-ARC); 3) AIDS Related Complex (ARC); and 4) Active AIDS. The last three stages may be present in combination with other infections, with central and/or peripheral nervous system disease, with associated autoimmune disease or with related neoplasm. All four stages are treated using the same basic method described herein. There are no patient inclusion or exclusion criteria for therapy. Patients in any or all of the four clinical stages of HIV-infection including history of exposure (i.e., $HIV^+$, Pre-ARC, ARC, and AIDS) are candidates for therapy.

The method of treating the HIV-infected patient begins with a panel of laboratory studies which include the quantitative evaluation of the activated peripheral blood mononuclear cell subsets, circulating viral proteins, cytokinases and soluble cell-surface receptors. The initial administration of a selected dosage of defibrotide is followed by incrementally increasing the dosage of defibrotide until a maximum tolerable dose is reached. The laboratory panel is repeated weekly during this therapy. These results together with the clinical markers of disease would indicate whether the defibrotide is efficacious and whether defibrotide should be continued to be given alone or with other therapeutic agents.

The details of treatment and the dose ranges fitting the various stages of the HIV disease will be expressed by retrospective analysis of respective laboratory and clinical markers. Additionally, dosage levels and frequencies as well as the use of other anti-HIV medication will also depend upon the individual patient or stage of disease and/or other concurrent medical conditions.

Before the initiation of therapy and weekly thereafter blood is drawn from the patient and subjected to a panel of tests which preferably include activated peripheral blood mononuclear cell subsets by two-color flow cytometry, lymphokines and soluble cell surface receptors by ELISA, and HIV-viral proteins by Western blot analysis. The peripheral blood mononuclear cell subset analysis will usually include either $CD4^+$, $CD8^+$, $CD19^+$, $CD25^+$, $CD56^+$, and HLA-DR alone, combined with one another, or combined with the quantification of monocytes. The Western blot protein tests include gp-24, gp-17, gp-120 and gp-160. The ELISA test measures TNF, sIL2R, sIL1 and soluble CD8. Every third week, it is preferred that cell cultures for HIV antibody neutralization, PCR and reverse transcriptase determinations be made.

HIV-I Gene Therapy in Accordance with the Invention

Gene delivery thus far has been a method by which foreign genetic material is introduced into a suitable target cell usually via viral vectors. Such strategy generally consisted of an ex vivo and an in vivo phase. In the ex vivo phase the foreign gene is inserted into target cells derived from the recipient. The engineered cells containing the newly inserted gene are expanded ex vivo. In the in vivo phase, the expanded engineered cells are transplanted into the recipient.

This modulatory therapy is the first of its kind which manages therapy from cell surface signaling to genomic modulation utilizing the oral and/or intravenous administration of nucleotides, without utilizing retrovirus, adenovirus or other gene viral vectors traditionally employed in gene therapy. Gene therapy has not, heretofore, been utilized without cellular transfection with viral vectors, and never before by oral or intravenous administration of nucleotides to humans.

Gene therapy has not, heretofore, been tried without the interaction of viral vectors, i.e., by the administration of nucleic acid-based pharmaceutical agents orally and/or by intravenous route. The prototype drug defibrotide, although administered to patients over the past 5–6 years, has never heretofore been contemplated for gene therapy. In addition, in other modalities of gene therapy, dosage has never been assessed by molecule markers. Molecule markers have never been defined within the system of secondary messengers, signal transduction systems, promoters (DNA sites which are on the same chromosome as the gene transcribed and to which RNA polymerase binds), enhancers (DNA regions that control a promotor from a great distance, sometimes as much as 30,000 bases), and transcription factors (diffusible regulatory proteins which bind to DNA transcription activation domains and regulate the rate of transcription by RNA polymerase).

HIV-disease has not been previously interpreted as a disease of dismodulation involving the genomes, cellular secondary messengers and cellular signal transduction systems. The specific pathways affected by the HIV-retrovirus have not been clearly delineated. Therapy of HIV-disease has not previously attempted to reclaim the affected cellular function systems from the virus by reversing the dismodulation at the various levels by using exogenous therapy involving various modulators of these systems.

The therapeutic approach of the invention disengages itself from the common practice of planning therapy based on clinical staging. The planning of therapy is based on the identified mismodulations of (a) membrane lipids and cytoskeleton; (b) cell-surface receptor/ligand interactions; (c) secondary messengers; (d) signal transducers; (e) cellular transcription factors utilized in viral replication: as well as based on the identified (f) oncogenes; (g) viral transcription factors; and (h) viral genomes. The method of therapy disclosed herein for HIV may also be used in treatment of other viral infections and neoplasms.

These mismodulations are classified into marker categories of (1) repair markers (items a–e) and (ii) disease markers (item f–h). The object of therapy in accordance with the invention is to (i) reestablish repair markers at the constitutively expressed tissue levels; and (ii) eliminate disease markers (in case of the oncogenes to reverse the transformation).

Irrespective of disease stage or clinical status the patient is screened with the complete panel of secondary messengers and signal transducers (repair markers), since all repair markers are biochemically interdependent. Repair markers reflect the underlying logic of transcriptional regulation. Therapy is aimed to concurrently induce some markers and suppress other markers. The prototype nucleotide if used at the correct doses (which are guided by the respective repair markers) can accomplish this goal.

Elimination of disease markers by the therapeutic nucleotide compound will occur at various levels. It can be an indirect phenomenon based on modulations of secondary messengers, such as cAMP; it can be a direct phenomenon based on modulations of the phosphorylation events involving genes and transcription factors. For example, cAMP activates protein kinase A enzymes, $Ca^{2+}$ activates protein kinase C enzymes, the prototype nucleotide up-regulates cAMP, and downregulates $Ca^{2+}$, or it can be a direct phenomenon based on modulation of cAMP responsive gene promoters (CREM, as enumerated above).

While not being bound to any specific mechanism of action, the following are proposed.

Proposed Mechanism A. Induction of sIL2R gene and HIV-I LTR are interdependent phenomena. If the protein kinase C dependent sIL2R gene is turned off by high cAMP levels, activation of HIV-I LTR is concurrently suppressed as well.

Proposed Mechanism B. Increased cAMP levels have been shown to induce viral replication (Nokta and Pollard, 1992, *AIDS Research and Human Retroviruses* 8(7):1255–1261). HIV-I REV/ENV genes are both phosphoproteins. There may be other routes for cAMP-induced replication of HIV-I. Although administration of the maximum efficacious dose will increase cAMP levels, prolonged administration of the nucleic acid at the maximum efficacious dose, so as to realize the successful administration of the maximum therapeutic dose would culminate in declining cAMP levels, since vWAg decreases on therapy if and once the maximum therapeutic dose is administered. Hence administration of the maximum therapeutic dose is paramount in overcoming cAMP induced viral replication. This phenomenon may at least partially, be based on the induction of protein kinase C, as a secondary biochemical event (i.e., protein kinase C induces sILR2 gene, which in turn modulates protein kinase C so as it can directly inhibit cAMP).

Proposed Mechanism C. The transcription factor NF-KB binds to both the HIV-I enhancer, and the sILR2 gene. Protein kinase C phosphorylates its inhibitor 1 kB and releases active NF-kB. Increased cAMP levels by inhibiting directly the $Ca^{2+}$ induced activation of protein kinase C would modulate this phosphorylation event, and downregulate the transcriptional activities related to NF-KB. Since NF-kB binds to both the HIV enhancer and IL2 receptor, increased cAMP levels will downregulate HIV-I replication.

Proposed mechanisms B and C show that increased cAMP levels can be both deleterious and beneficial. It can be clearly seen that the prototype nucleotide is an overall "downregulator" of biochemical events, if maximum therapeutic and efficacious dose levels are administered.

It has now been discovered that the co-administration of various anti-sense or missense nucleic acids with, for example, defibrotide, would (1) alleviate the complication of cAMP induced viral replication; (2) induce inhibition of viral replication mediated via modulations of cAMP, protein kinase A, protein kinase C, cellular redox state, G-proteins, or cAMP induced gene promoters (in this regard, defibrotide and other nucleotide derivatives introduce for the first time into anti-HIV therapy nucleotides with no sequence specificity that concurrently modulate the totality of the cellular second messenger/signal systems for rapidly transducing extracellular signals into specific patterns of gene expression in the nucleus); (3) concurrently induce inhibition of viral replication with sense, anti-sense, or missense nucleic acids (e.g., DNA, mRNA, DNA/RNA ribosomes, inhibitors of viral protease, viral integrase); and (4) introduce a modality of gene therapy (i.e., genetic engineering) which can be safely administered to humans, which does not utilize viral vectors, which can be administered either intravenous or orally, which enables administration of sequence specific combination of nucleic acids adjusted specifically to the selected parts of the HIV-genome and cellular repair pathways, which adjust the dose so as to modulate selected genes or cellular/viral molecules, which enables the most efficient administration of various different nucleotides with differing cellular uptake dynamics and chemical anti-viral potencies, and which administers excess DNA to enable the self-integration of DNA.

This process is superior to present viral vector directed gene therapy and would also enable competitive inhibition of proviral integration, and/or dislocation of the integrated pro-virus. Cellular uptake dynamics would directly define the anti-viral and genetic modulatory capacities of each respective nucleotide. Nucleic acid derivatives having chemical modifications are as described previously (e.g., nucleotides conjugated with poly(L-lysine) or which is modified by, for example, the addition of amino acids such as lysine, histidine and arginine, the addition of optimum concentrations of folate and/or biotin, the addition of the optimum ratios of metals and ions including zinc, manganese and iodine, by the addition of 5'-polyalkyl moieties, cholesterol, vitamin E, 1-2-di-0-hexadecyl-3-glyceryl and other lipophilic moieties and/or modified by the replacement of phosphodiester bonds with phosphothiotate bonds) and combination nucleic acids would be employed.

Combination nucleic acids will, hereinafter, be referred to as "combo-nucleic acids". Combination of sequence nonspecific prototype nucleic acids (e.g., defibrotide and derivatives thereof) with various sequence specific nucleotides has never, heretofore, been proposed for use as a multimodal therapy for HIV.

Various sequence specific nucleotides, such as TAR decoy RNA, negative mutants of the viral REV transactivator, synthetic promoters with the consensus sequence for binding of the transcription factor Spl, and the TATA box, TAT mutants, mutations involving the seven cysteine residues, REV mutants, NEF-cDNA sequence with or without U3 region sequence of the 3'LTR, HIV-I LTR enhancer (−137 to −17) mutant, HIV-I LTR sense sequence of the negative regulatory element (−340 to −185), LTR Spl (GC box) binding site and TATA box mutants and LTR GAG gene sequence mutants, are known in the prior art. However, such sequence specific nucleotides have been used only in the in vitro setting as "single mode" anti-viral agents, the mode of actions being limited to the sequences.

Examples of combo-nucleic acids are listed below:
a) defibrotide sequence+TAR decoy RNA,
b) defibrotide sequence+negative mutants of the viral REV transactivator,
c) defibrotide sequence+synthetic promoters with the consensus sequence for binding of the transcription factor Sp1, and the TATA box,
d) defibrotide sequence+TAT mutants, mutations involving the seven cysteine residues,
e) defibrotide sequence+sense derivatives of CIS acting negative elements (CRS) present in the integrase gene+REV mutants,
f) defibrotide sequence+transdominant suppressor of REV (mutations involving amino acid 78 and 79),
g) defibrotide sequence+NEF-cDNA sequence with or without U3 region sequence of the 3'LTR,
h) defibrotide sequence+POL reverse transcriptase gene mutants,
i) defibrotide sequence+POL viral integrase gene mutant,
j) defibrotide sequence+POL viral protease gene mutant,
k) defibrotide sequence+HIV-I LTR enhancer (−137 to −17) mutant,
l) defibrotide sequence+HIV-I LTR sense sequence of the negative regulatory element (−340 to −185),
m) defibrotide sequence+LTR NFKB mutant (−104 to −80),
n) defibrotide sequence+LTR Spp1 (GC box) binding site and TATA box mutants,
o) defibrotide sequence+LTR GAG gene sequence mutants,
p) defibrotide sequence+ENV, GAG, POL gene sequences placed 3' of the REV mutant codon, and
q) defibrotide sequence+host DNA sequence of preferred targets for proviral integration.

The sequence nonspecific chemical derivative in the combo-nucleic acids exemplified above are preferably also modified for improved cellular uptake, and enhanced anti-viral activity with the chemical modifications described above.

Therapy/Laboratory/Clinical Markers

Clinical markers consist of any and all disease markers noted on physical examination, without restriction. Clinical laboratory markers consist of any and all noted clinical laboratory abnormalities, without any restrictions. While one skilled in the art would readily recognize which markers are indicative of a pathological state to follow, the following list is, in addition to those listed above (i.e., Panels 1–11), provided as a guideline.

Panel 11: Peripheral HIV 1 Panel

HIV-1 rgp 160 (glycosylated full length protein);
HIV-1 rgp 120 (Binds to CD4+cells and inhibits syncytia;
HIV-1 p121 (immunodominant region of gp41);

HIV-1 pg2 (amino acid from core proteins p24 and p15);
HIV-1 GAG5 (amino acids from core protein p24);
rs CD4 (fully glycosylated, binds to $gp12_0$ and inhibits syncytia);
Anti gp120 MAb 1C1 (Io, $G_{2A}$ antibody reacts with gp120);
Anti gp41 MAb 2A2 ($IgG_{2A}$ antibody reacts with gp41);
Anti V3 Loop Mab 50.1 (Binds to principle neutralizing determinant of HIV);
HIV antigen p24;
reverse transcriptase;
syncytia formation;
cytopathic effect;
plaque formation, Panel 12: Repair Marker Panel
Intracellular platelet/PBMNC;
vWAg (preferably mRNA pro-vWAg);
cAMP (endogenous and PMA stimulated);
cGMP (endogenous and PMA stimulated);
glutathione;
GTP/GDP;
GAP;
RpA 1 (small G protein);
p 21 ras (G protein group);
v-nef (viral G protein);
Gs 1 Alpha/ Gi 1 Alpha;
oxygen radicals;
NADP/NADPH;
$FAD/FADH_2$;
$Ca^{2+}$ (endogenous, IL2/PHA stimulated);
1,2 diacyglycerol (DAG, endogenous, IL2/PHA stimulated);
Inositol triphosphate (IP 3, endogenous, IL2/PHA stimulated);
NF-kB.

EXAMPLES

Example 1

To measure the effect of defibrotide on HIV it was first necessary to label the drug and determine whether defibrotide will enter the nucleus of the human cell. Knowing the phosphodiester linkages in defibrotide, its comparative nuclear penetration was assessed by labelling defibrotide with a photo-activatable analogue of biotin. The biological activity of defibrotide after labelling was considered to have been preserved since published data shows that previous oligonucleotide probes have been labelled with conjugates and still remained biologically active. Image analysis utilizing a cold CCD camera revealed that uptake of defibrotide was localized in the nucleus. This supports the hypothesis that the mechanism of efficacy for defibrotide is largely contributed to by its modulatory activity on the genetic material of the cell, no matter what disease entity is being treated. As shown in FIGS. 2 and 3, the nuclear uptake of defibrotide is directly proportional to the concentration of defibrotide with biotin. The observed uptake supported the increased efficacy of defibrotide with the larger doses used, and also supports the hypothesis that at critically high dose levels various previously unknown different effects of defibrotide can be seen. It was also observed that uptake by monocytes was significantly greater than that by lymphocytes.

The cellular uptake of defibrotide without biotin and labelled with cyanine dye Cy5. 18 was also measured. It was observed that biotinylation of defibrotide enhanced the cellular uptake of defibrotide in the lymphocyte population. However, there was no difference in uptake between monocytes incubated with biotinylated or fluorescently tagged defibrotide. This can be seen by comparing FIGS. 4 and 5.

Example 2

To further confirm the specificity of defibrotide for the treatment of HIV infection, HIV infected peripheral blood mononuclear cells with varying doses of defibrotide were evaluated by staining for all viral envelope proteins using concanavalin A (Con-A) stimulated and unstimulated cells (Anti-HIV 1, and Anti-HIV 3 specific Anti-HIV antibody). The blood sample was obtained from a patient using an evacuated blood collection tube containing sufficient EDTA to prevent coagulation of the sample.

Mononuclear leukocytes (white cells) were obtained by layering a 1:1 (volume:volume) blood to RPMI 1640 tissue culture medium (Grand Island Biological Co.) aliquot over histopaque (d=1.077, Sigma Chemical Co.) under sterile conditions. The white cell population was suspended in a solution of the RPMI 1640 medium supplemented with 10% heat-inactivated fetal calf serum and gentamicin, at the concentration of 5 micrograms/milliliter. The white cells were then concentrated to a level of two million cells per three milliliters ($2 \times 10^6$ cells/3 ml) of the above solution. The white cells were collected in flat-bottomed microtiter containers (Cell Wells, Corning).

The cell populations were further divided into two groups. One group received stimulation by Con-A, the other group remained unstimulated by Con-A. Con-A stimulation enhances the uptake of the antibody-dye label by HIV-contaminated cell components, thereby demonstrating an increase in the expression of the HIV protein.

Subpopulations of unstimulated and stimulated white cells were then incubated in the presence of discrete concentrations of defibrotide. Each successive assay employed successively greater concentrations. A control sample of incubate containing no defibrotide was also prepared. A labelling antibody solution was prepared by directly conjugating Cy5. 18 with human α-HIV antibody to a final dye/protein ratio of 5.0 (α-HIV-Cy5.18).

The cell subpopulations were again divided into two groups, one group for intracellular antibody labelling, and one group for surface antibody labelling. Cells reserved for intracellular labelling were fixed with 70% ETOH, washed twice with monoclonal wash, and then resuspended into a solution containing 200 microliters of Hank's balanced salt solution (HBSS), supplemented with 2% FCS and 0.1% sodium azide (monoclonal wash) and 5 microliters of α-HIV-Cy5.18 solution. The entire cell preparation was incubated for 45 minutes at 4° C. The cell preparation was then washed twice with the monoclonal wash, and resuspended in 1% paraformaldehyde.

Cells reserved for surface labelling were prepared by washing twice in monoclonal wash to which 5 microliters of α-HIV-Cy5. 18 have been added. Next, 20 microliters of specific surface glycoprotein monoclonal antibody was added to the incubation solution. The surface glycoprotein antibody solution contained CD3-FITC (heterogenous T-cell antibody conjugated with fluorescein isothiocyanate dye) and CD4-RPE (helper T-cell antibody conjugated with phycoerythrin dye) obtained from Becton-Dickinson.

All cells thus prepared were then analyzed using a Becton-Dickinson FACS 440 dual laser (argon/krypton)

flow cytometer. The expression of HIV proteins was determined on a per-cell basis. Fluorescence was measured on a logarithmic scale but converted to a linear scale for analysis.

Figure 7:
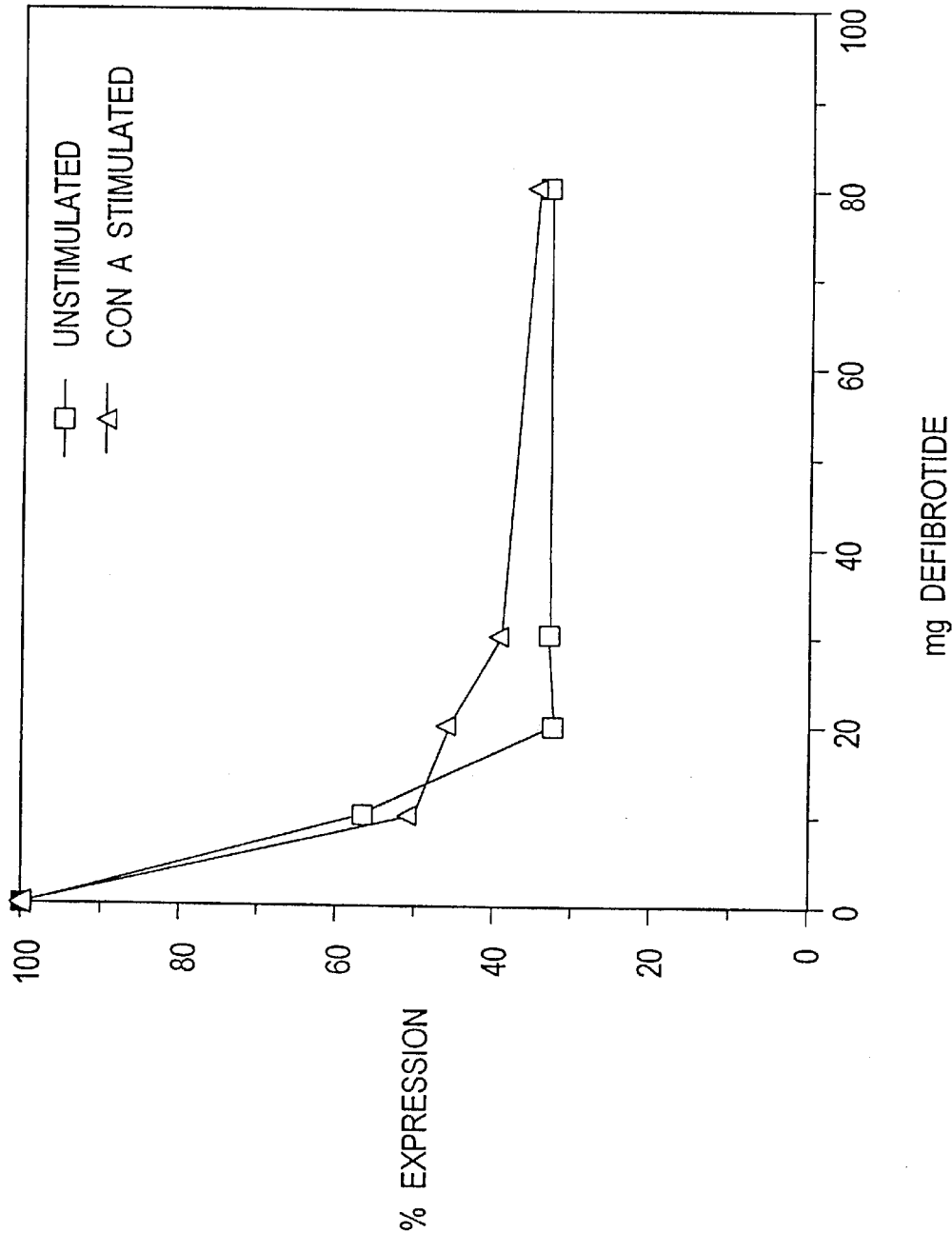
FIG. 7 is a graph showing the percent expression of HIV viral proteins remaining when blood lymphocytes of an HIV infected individual were exposed to various doses of defibrotide with and without Con-A stimulation.
Figure 8:
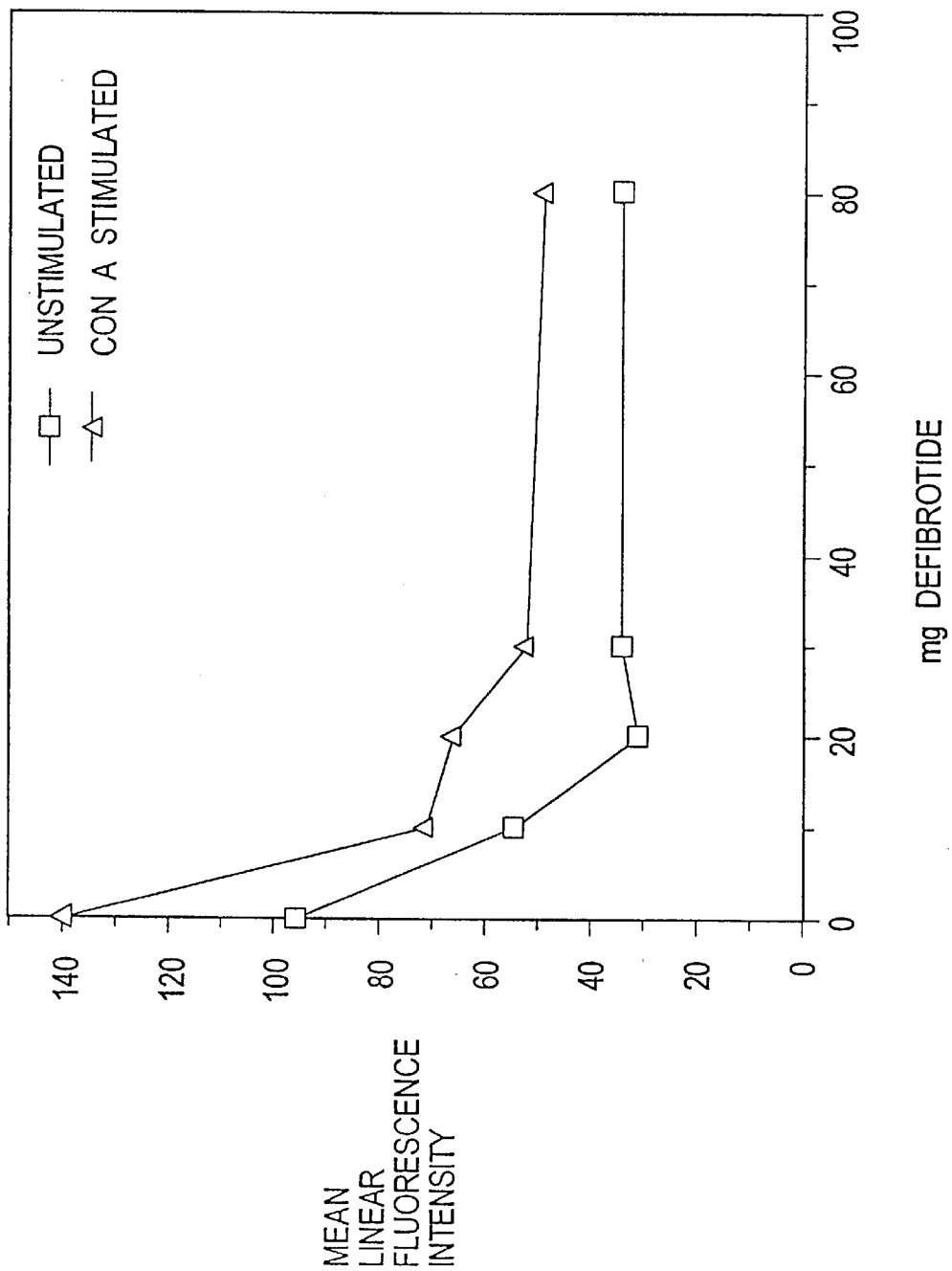
FIG. 8 is a graph showing the laboratory response expressed in terms of mean linear fluorescence intensity of the peripheral blood mononuclear cells of an HIV infected individual, the cells being subjected in vitro to varying levels of defibrotide using a cell culture assay technique with and without Con-A stimulation.

FIG. 7 shows HIV protein expression at selected dosages. Assay results for the same sample shown in FIG. 8 are in terms of the intensity of the fluorescence of certain antibody-labelled mononuclear leukocytes (Mean Linear Fluorescence Intensity). Fluorescence intensity is proportional to HIV protein expression, and thus the activity of HIV. It is seen that the expression of the HIV proteins decreases and then levels off with increasing concentrations of defibrotide.

Before administration of defibrotide, Con-A stimulated cells expressed 32% more viral proteins. However, after administration of 20 mg of defibrotide, both stimulated and unstimulated cells express 70% less viral proteins. At 30 mg concentration of defibrotide in both Con-A stimulated and unstimulated cells the expression of viral proteins leveled off. This supports the specificity of defibrotide for HIV-virus as well as the fact that if cells are induced to divide, translating into proliferation of the virus, more HIV virus can be killed, albeit, at higher doses.

Example 3

Patients with various diseases of vascular prothrombotic backgrounds were treated with escalating dose levels of defibrotide. A variety of coagulation and hematological assays with other molecular markers of inflammation, etc., were conducted on blood samples drawn from the patient before and after each dose escalation. From an analysis of the test results and clinical observations, it was discovered that certain effects of defibrotide lead to a remission state of certain specific aspects of disease states corresponding to the various dose ranges employed.

As an example, hematological recovery in thrombotic microangiopathy, generally, yet not exclusively, occurred when the patient received doses of defibrotide ranging from 20 to 30 mg/kg/day. These doses however did not cure the renal lesions since creatinine levels remained above normal (or only partially corrected) at the dose levels where hematological recovery was complete. Renal recovery evidenced by normalization of creatinine levels occurred between 40 and 250 mg/kg/day.

Even in the presence of normalization of creatinine levels (the conventional criteria of complete recovery) it was observed that complete remission was yet to be reached by the observation of elevation of blood pressure, low AgTPA and high fPAI levels. Therefore, doses of defibrotide continued to be increased until blood pressure levels became normal. The dose elevation not only treated blood pressure, but also led to further improvement of creatinine. Thus, treatment with marker-dependent doses, applied correctly, led to a state of "cure".

Example 4

In a normal individual, it was determined that increasing the DKGD dose does not induce any elevation in the vWAg since there is no ongoing repair process, i.e., no disease state. Doses administered to a normal individual, in contrast to the doses given to an individual exhibiting a pathological disease state, will not induce any alteration in vWAg levels, i.e., defibrotide will not induce transcriptional activity at the genomic level. vWAg predicts the transcriptional rate of the respective repair molecules induced by the nucleotide and will guide the assessment of maximum efficacious dose and maximum therapeutic dose.

The minimum value of the vWAg level among a group of disease patients ("minimum highest value") was monitored when defibrotide was administered at a daily dose within the range of 10–400 mg defibrotide/kg/day (DKGD). Each increase in DKGD increases the preceding minimum highest value of vWAg by an increment smaller in each successive interval. Using defibrodde, the highest percentages of increments were found to occur at the borderline of 40 DKGD. Increasing DKGD above 400 induces only negligible improvements over levels below this dose. In practice, this is the dose level above which complications of bleeding have been observed by the inventor with high molecular weight defibrotide.

Typically, escalation to a new DKGD range will induce escalation of transcriptional activity for the universal marker vWAg within a period ranging from 1–9 days to 13–58 days. The higher the DKGD the longer it will take to increase the transcriptional activity over the previous dose range. A higher dose range, however, will show a more prompt and more significant increase in transcriptional activity if compared to lower dose range, both being initiated on the first day of therapy.

If two patients exhibiting the same disease state are treated at different maximum daily dose levels, dose dependent remission would be observed.

Examples 5–7

Examples 5–7 report the treatment of three HIV infected patients. These patients were all treated in Turkey with defibrotide obtained from CRINOS. In Tables I–VI, below, the following are the normal laboratory ranges: IL-1=3.6 pg; IL-2=4.3–4.8 pg; IL-6=7.1–7.3 pg; TNFα=25.1–26.3 pg; cAMP=0.4–0.6 nM; CGMP=0.85–0.95 nM; normal cGMP/cAMP=2.125; $\beta_2$-microglobulin=<1900 µg/l.

Example 5

A 28-year old white HIV$^+$/ARC male exhibiting waste syndrome, Herpes labialis and Herpes genitalis associated with widespread tissue damage, oral/pharyngeal candidiasis, polyarthralgias and tuberculosis was treated with defibrotide.

On Day 1 of treatment, a 360 mg/kg IV bolus of defibrotide was administered. Thereafter, a dose of 160–275 mg/kg/day was administered. Defibrotide was administered 86 days out of a 118 day treatment course.

Progressive increase in weight and amelioration of diarrhea was observed throughout the therapy period, a total weight gain of 12 kg occurring during the treatment period. Improvement in Karnofsky performance score stated at day 3 and increased from a score of 3 to a score of 10 over the treatment period.

The effect on artralgia was observed by the third consecutive day of treatment and was found to be strictly dose dependent. Upon cessation of therapy arthralgia relapsed to original condition and entered remission upon reinitiation of DNA therapy.

The effect on Herpes began on day 4 of treatment. By day 36 of the treatment period, genital Herpes lesions were in complete remission. By day 68, Herpes labialis lesions were in complete remission. No relapses were seen with temporary cessation of defibrotide.

Tables I and II summarize pertinent laboratory markers.

TABLE I

| TIME (days) | Absolute Lymphocyte | CD4 % | Absolute CD4 | CD8 % | Absolute CD8 | $B_2$-micro-globulin |
|---|---|---|---|---|---|---|
| 1 | 1388 | 13.2 | 183 | 22 | 305 | N.D. |
| 26 | 1152 | 32.0 | 369 | 50 | 576 | N.D. |
| 90 | N.D. | N.D. | N.D. | N.D. | N.D. | 3582 |
| 104 | N.D. | N.D. | N.D. | N.D. | N.D. | 1348 |
| 118 | 3300 | 21.0 | 693 | 32 | 1056 | N.D. |

* N.D. = not determined

TABLE II

| TIME (days) | IL2 | TNFα | IL6 | cAMP | cGMP | cGMP/cAMP |
|---|---|---|---|---|---|---|
| 8 | 14.3 | 30.1 | 41.6 | 2.0 | 1.03 | 0.52 |
| 76 | 7.3 | 14.7 | 3.7 | 3.65 | 2.10 | 0.58 |

Elevated cAMP/cGMP was observed at the onset of therapy, signifying activation of both protein kinase A and protein kinase C pathways. A progressive rise in absolute and T lymphocyte numbers, CD4 and CD8 was seen. A decrease in IL1, IL-2, IL-6 and TNF-A was observed during treatment.

Complete remissions in accompanying disease states include Herpes labialis, oropharyngeal candidiasis, arthralgia, and Herpes genitalis as well as accompanying tissue damage. Complete normalization of TB findings (Chest x-ray) with apparent radiological remission occurred.

Example 6

25-year old white HIV+ female was treated with defibrotide. At the onset of therapy, the patient was asymptomatic but had a low CD4 count.

On day 1 of the treatment, a 200 mg/kg IV bolus of defibrotide was administered. Thereafter a dose of 150–275 mg/kg/day was administered. Anabolic effects of the DNA were seen by day 13.

DNA therapy was terminated after 29 days secondary to a rise of CD4 percent and absolute counts. DNA therapy was reinitiated 25 days later secondary to a decline in CD4 percent and absolute counts. Therapy was continued on an outpatient basis, intravenous administration being alternated with oral administration.

Tables III and IV summarize pertinent laboratory data. In this patient, all tested interleukin levels were normal.

TABLE III

| TIME (days) | Absolute Lumphocytes | CD4 % | Absolute CD4 | CD8 % | Absolute CD8 | $β_2$-micro-globulin |
|---|---|---|---|---|---|---|
| TREATMENT CYCLE #1 | | | | | | |
| 1 | 973 | 15.2 | 148 | 20.1 | 196 | N.D. |
| 28 | 1100 | 48.0 | 528 | 50.0 | 5.50 | 3300 |
| TREATMENT CYCLE #2 | | | | | | |
| 1 | 429 | 34.0 | 146 | 22.0 | 94 | N.D. |
| 20 | 1945 | 15.0 | 292 | 20.0 | 389 | 2468 |
| 56 | 2600 | 29.0 | 754 | 20.0 | 520 | N.D. |

TABLE IV

| TREATMENT CYCLE #2 | | | |
|---|---|---|---|
| TIME (days) | cAMP | cGMP | cGMP/cAMP |
| 1 | 1.25 | 0.98 | 0.78 |
| 8 | 1.55 | 3.00 | 1.94 |
| 20 | 1.50 | 3.40 | 2.27 |

Treatment was characterized by increases in CD4, CD8, total lymphocyte, total T-lymphocyte counts accompanied by elevations in cAMP and cGMP, and in therapy related decreases in IL-6 and TNF-α. A total weight gain of 7 kg was observed.

Example 7

A 33-year old white male with AIDS and opportunistic infections including Herpes labialis associate with necrotic lesions, oral/pharyngeal candidiasis, tuberculosis and crytococcal diarrhea.

On day 1 of treatment, a 200 mg/kg IV bolus was administered. Treatment at a dose of 100–250 mg/kg/day was continued until day 40. The lower doses being given on days 7–13 having been reduced secondary to prolonged APTT. Treatment was thereafter discontinued due to unavailability of the drug. The patient died 8 days following cessation of therapy.

An anabolic effect was seen from day 6. Diarrhea was controlled from day 3 and cultures for cryptococcus became negative on day 15. Lesions of the lip began healing on day 5 and were completely healed by day 18. Odynophagia improved from day 5. Performance score began improving by day 3, reaching an optimum level of 5 between days 16 and 21.

Tables V and VI summarize pertinent laboratory data.

TABLE V

| TIME (days) | Absolute Lymphocytes | CD4 % | Absolute CD4 | CD8 % | Absolute CD8 |
|---|---|---|---|---|---|
| 7 | 700 | 10.0 | 70 | 29.0 | 203 |
| 18 | 800 | 10.0 | 80 | 17.0 | 136 |
| 44 | 700 | 8.0 | 56 | 14.0 | 98 |

TABLE VI

| TIME (days) | IL1 | IL2 | TNFα | IL6 | cAMP | cGMP | cGMP/cAMP |
|---|---|---|---|---|---|---|---|
| 21 | 105 | 18.0 | 95.1 | 40.6 | 1.4 | 1.1 | 0.79 |
| 33 | 85.5 | 7.6 | 14.8 | 45.1 | 1.5 | 0.96 | 0.64 |

Decline in elevated IL-1, IL-2 levels and complete normalization of TNF-α levels was observed. An increase in I1-6 was seen with cessation of therapy. At the time of death, a 3 kg weight gain was observed, and Herpes labialis and oral/pharyngeal candidiasis were in complete remission.

Example 8

The best and most efficacious clinical application of defibrotide and other polynucleotides is as pharmaceutical cell modulators committed to revival of normal cell function. The doses and the markers will vary among diseases. Moreover, the markers for any given disease will frequently vary among different stages of the disease. The aim of treatment is the irreversible normalization of a marker or markers. Once this is obtained, a subsequent marker for the lower disease activity will be sought and treated. The possibility of cure depends on the identification of appropriate markers. The selection and use of markers to determine doses can be best understood with reference to selected patient data presented hereafter as representative examples of patients suffering from thrombotic microangiopathy (HUS), prothrombotic states of neoplastic chemotherapy induced or immunological (anti-phospholipid antibody) etiologies, deep vein thrombosis, and soft tissue necrosis, as well as acquired platelet function abnormalities. Incidental therapeutic effects of defibrotide in these patients also involved pulmonary (e.g., adult respiratory distress syndrome (ARDS)), cardiac (e.g., subendocardial myocardial infarction) and renal systems (e.g., glomerular proteinuria). There is an optimum level of transcriptional activity induced that is specific for each patient. This level depends on maximum efficacious dose, acuteness and degree of injury, and specificity of the nucleotide for the treatment.

The pathological states exhibited prior to therapy of patients Nos. 4–14, as well as the condition exhibited following therapy, are summarized below. All patients treated were resilient to conventional therapy and considered to be, at the time of treatment with defibrotide, moribund.

Patient No. 4
Initial Pathological State
Primary anti-phospholipid antibody syndrome with clinical components of end stage renal disease on dialysis, adrenal insufficiency, mitral insufficiency, immunological prothrombotic state (secondary to presence of the anti-phospholipid antibody), bilateral femoral thrombi, GI-tract ischemic necrosis (as the terminal event after cessation of the nucleotide therapy), uremic pericarditis, acquired thrombopathy with ecchymoses and soft tissue hematoma, nephrogenic hypertension.
Result of Therapy
The patient showed a transient decline in endothelin-I levels with a rise in DKGD from 60 to 160 mg/kg/day which was concurrent with onset of urine flow. Rise in DKGD to 160 mglkg/day was also concurrent with rises in AgTPA and increased conversion of protein CI to protein SI which accompanied the clinical markers of the lysis of left femoral thrombus and amelioration of prothrombotic tendency during dialysis, respectively. From the patient response, the conversion of protein CI to protein SI was postulated to be inhibited by anti-phospholipid antibody, which inhibition was reversed by the nucleotide therapy.

The patient showed the immunosuppressive effect of the nucleotide over inhibition of the protein kinase C pathway and possibly also via hybridization with the sIL2R genomic sequence. In this regard, activation of the sIL2R is known in the art to occur via protein kinase C pathway induced phosphorylation of transcription/translation related factors/molecules. Decline in DKGD to 100 mg/kg/day on day 35 was concurrent with recurrent increase in the sIL2R level while reinitiation of therapy at 150–200 mg/kg/day dose on days 41, 42, 43 was concurrent with complete normalization of sIL2R level. Acquired thrombopathy represented by impaired platelet aggregations of ADP 5 and arachidonic acid, were reproducibly responsive to the administration of the nucleotide starting at 60 mg/kg/day dose levels and concurrent with the clinical disappearance of ecchymoses and subcutaneous hematoma.

Successfully treated clinical/laboratory entities in this patient were prothrombotic state secondary to anti-phospholipid antibody unresponsive to all other pharma-acquired thrombopathy and nephrogenic hypertension as well as successful thrombolysis at the site of the infusion of the nucleotide.

Uremic periconditis initially contemplated to be secondary to high uric acid load possibly as a result of the nucleotide administration was subsequently not correlated with the administered amount of the nucleotide. However, in uremic patients careful follow-up of uric acid levels are recommended.

Patient No. 5
Initial Pathological State
Rejection, nephrogenic hypertension, recurrent hemolytic uremic syndrome in transplanted kidney microangiopathic hemolysis, consumptive thrombocytopenia.
Result of Therapy
There was complete, biopsy proven cure state of the hemolytic uremic syndrome as the result of therapy with the prototype nucleotide. At the time of rejection, the biopsied organ histologically and by electron microscopy showed complete absence of haemolytic uremic syndrome findings. The disease markers in this patient were (contrary to patient No. 4) elevated levels of both Protein CA and Protein SI, reflecting optimum secretion by the respective cells of these anti-thrombotic molecules, clearly as a response to the existing lesion of the thrombotic microangiopathy. With the amelioration of the lesion of thrombotic microangiopathy both molecules descended to normal levels. Renal disease specific disease markers were creatinine and endothelin-I, each of which showed concurrent normalization with the administration of the nucleotide. With declining dose levels, the more crude marker of creatinine stayed normal; however, the more refined marker of endothelin-I escalated to abnormal levels.

Rejection of the transplanted organ was not therapeutically pursued in this patient. Had this patient been treated for the endothelin-I disease marker, the vascular endothelial cell lesion of the rejection process would have been prevented. In addition, if any of the repair markers proposed herein had been followed, complete prevention of the rejection process would have been feasible.

The consumptive thrombocytopenia and hemolysis were irreversibly treated. Dose dependent responses of elevated sIL2R and NK (National Killer cell) levels due to the nucleotide where shown.

This patient was treated at a very acute stage of the renal/hematological lesions. More acute lesions with longer injury parameters will respond to lower doses of the nucleotide, as shown in this patient. In contrast to patient No. 4, the lower doses are much less effective in the immuno-suppressive effect of the nucleotide, which is proposed to have a direct genetic regulatory component in the multimodal HIV treatment by this nucleotide and its derivatives. As with patient No. 4, all the disease markers normalized with the increasing levels of the universal marker vWAg.

Patient No. 6
Initial Pathological State
Mitomycin C-induced hemolytic uremic syndrome.
Result of Therapy
This patent presented the opposite case from patient Nos. 4 and 5. Increasing levels of AgPAI1, endothelin-I, failure of correcting protein SI levels, failure of correcting NK levels, collectively represent the therapeutic inefficacy of the nucleotide both in a quantitative as well as in a qualitative sense when doses less than 40 mg/kg/day are utilized.

Patient No. 7
Initial Pathological State
Primary anti-phospholipid antibody syndrome, immunological prothrombotic state, post-phlebitic syndrome, bilateral femoral thrombi, bilateral soft tissue necrosis of digits, hypertension, nephrotic syndrome, subendocardial myocardial infarction, mitral valve prolapse, acute respiratory distress syndrome, lupus anti-coagulant.
Result of Therapy
Analogous to patient No. 4, this patient's clinical syndromes were secondary to an intractable prothrombotic state based on the circulating lupus anti-coagulant, and IgG/IgM anticardiolipin anti-phospholipid antibodies. While patient No. 4 had many irreversible tissue damage components, patient No. 7 represent a complete cure state for all of the clinical aspects of the disease state.

Effective doses corresponded to significant elevations in the universal marker vWAg which was accompanied by corrections in the disease markers. Expression of the presence of the lupus anti-coagulant in the prolongation of APTT was ameliorated for the duration of therapy with the nucleotide. Increasing levels of vWAg on adequate doses was correlated with declining levels of APTT. Also noted was the fact that after cessation of the nucleotide therapy serological findings of the lupus anti-coagulant (i.e. prolonged APTT, low FX1 activity, and low FX11) had recurred. However, corresponding thrombotic complications of tissue damage remained in remission. Anti-phospholipid antibody induced prothrombotic states may involve various pathways. In patient No. 4 one of these pathways was clearly by the nucleotide corrected failure of activation of protein SI. Before-therapy and after-therapy normal levels of these antithrombotic molecules shown in patient No. 7 clearly negated involvement of the protein CA/CI pathway.

Significant "reductions" in the levels of these two proteins on therapy and at the height of the antithrombotic effect by the nucleotide were observed. In contrast to what has been shown in the prior data, nucleotides will not induce uniform pharmacological actions in every patient reproducibly, as shown herein by the nucleotide induced increase in the initially low levels of protein SI in patient No. 4 (same disease state) and nucleotide induced decrease in the initially elevated/normal levels of protein SI in Patient No. 7. Since in both cases an antithrombotic effect was successfully obtained, the nucleotide is not acting in an erratic manner. Hence the pharmacological actions of the nucleotide are defined by the presence and type of the abnormality.

The initially normal level of TNF was elevated between days 28–38. This period was concurrent with the development of acute respiratory distress syndrome and myocardial infarction with conduction defect cell lesion. Noted are clear, inverse relationship of increasing vWAg levels with declining AgPAI1, and endothelin-I levels, a repeatedly observed phenomenon governing the behavior of vWAg with the modulation of any disease marker in either direction in any one patient. Decline in AgPAI1 shows it to be a representative marker of endothelial cell injury/repair phenomenon rather than a marker of effective fibrinolysis, since its behavior is not accompanied by increasing AgTPA levels. Furthermore this patient did not display any increased fibrinolytic activity with reference to the dissolution of various thrombi in his vasculature. As in Patient No. 5, at the time of the most extensive and acute lesion, transcriptional/transitional modulatory repair event by the nucleotide was at its peak, represented universally in the transcriptional modulation of vWAg. On no other chemical therapy, but only on defibrotide, ARDS lung findings and subendocardial myocardial infarction enzyme and electrocardiogram findings completely reversed by day 51, accompanied by the precipitous drops in AgPAI1, and endothelin-I, levels both molecules being disease markers for any type of endothelial mitral valve prolapse and ventricular wall dysfunction (documented by EKG and echocardiograms). These events occurred between days 35–38 while off therapy with defibrotide. The events were etiologically/temporally related to infusion of streptokinase. Nucleotide therapy was reinitiated at 60 mg/kg/day dose (day 38) escalated to 80 mg/kg/day dose (days 38–41), followed by 100 mg/kg/day dose (days 41–50), decreased to 80 mg/kg/day dose (days 50–53), and finally completely discontinued from day 53 on. Follow-up without therapy was until day 275.

By day 39 vWAg reached its peak of 9.2 u/ml, (in keeping with this text's statement that all thrombi were old and established). Hence high levels of both AgTPA and AgPAI1, between days 0 and 25 also are an expression of endothelial cell lesion which is irreversibly corrected by the nucleotide. Resolution of the anti-phospholipid antibody related myocardial infarction, acute respiratory distress syndrome, leak proteinuria/nephrotic syndrome (24 hour urine protein declined from 13,300 mg/24 hrs. to 218 mg/24 hrs.) were concurrent with the serological disappearance of the anti-phospholipid antibody. Also concurrent with the clinical case states, including prothrombotic state, was the correction of the acquired thrombopathy, reflected in impaired platelet aggregations.

This patient showed therapeutically successful human doses of defibrotide in the modulation of redox-state, NADP/NADPH, FAD/FADH$_2$ oxidative phosphorylation pathway, the so-called "cytotropic" action of the drug. The clinical corresponding pictures of soft-tissue necrosis and deep vein thrombosis as well as post-phlebitic syndrome were irreversibly, completely cured.

For the first time, as is clear from patient No. 7, it has been shown that resolution of occluded proximal circulation is not a required event for tissue healing in any or all thrombotic events. The disease states encompassing the totality of microvascular pathology states can be treated with nucleotides. Heretofore, disease states with tissue damage associated with compromised circulation, have been treated only for or on the basis of elimination of the thrombi.

Patient No. 7 showed complete healing of the totally necrotic digits involving both hands. Repeated arteriograms done for planned microvascular by-pass surgery have shown absolutely no improvement with the vessels (if anything, some worsening)—a finding that accompanied complete healing of the ischemic/necrotic tissues with no sequelae whatsoever.

Total healing of the tissue was completed around day 100 of the follow-up, nucleotide therapy having been discontinued altogether by day 53.

Disease parameters of this patient remained normal off therapy up to day 253 follow-up.

Patient No. 8
Initial Pathological State
Microangiopathy hemolysis, consumptive thrombopathy, hemolytic uremic syndrome/clostridium difficile toxin, lupus anti-coagulant, nephrogenic hypertension, anuric renal failure.
Result of Therapy
This patient developed within a time period of 8 days after ingesting raw meat *Clostridium dificile* related Hemolytic Uremic Syndrome. At the onset of therapy with the nucleotide she was completely uremic, on dialysis, thrombocytopenic, anemic with leucocytosis, hypoalbuminemia and onset of anemia. As with many a patient with HUS she also had a circulating lupus anticoagulant. Low protein SI levels secondary to anti-phospholipid antibody emergence between days 9 and 33; declining protein CA levels signified increased usage thereof with its activation of protein SI (nucleotide mechanism of efficacies are as electron donor to Vitamin K, amelioration of anti-phospholipid antibody induced lipid peroxydation). Activation of protein SI by activated protein CI was seen.

Amelioration of consumptive thrombocytopenia with the nucleotide administration was seen as well as associated thrombopathy with under-regulation of Adenosine $A_1/A_2$ receptors and related impairment of prostanoid synthesis (i.e., $PgI_2$). Thrombocytopenia was confirmed as being "consumptive", i.e. secondary to increased destruction via platelets' increased aggregations to the injured endothelial cell, all reversed with the nucleotide.

It is noted here that within the concept of "antiplatelet therapy" there is no pharmaceutical agent yet identified until the present text which reverses the "irreversible aggregation of platelets" as represented here by the impaired ADP 20 induced platelet aggregations.

Complete correction of serum creatinine levels which are also concurrent temporally with the correction of consumptive thrombocytopenia and hemolysis was observed.

At the time of discharge, this patient had normal urine flow, was off dialysis, and had normal platelet counts. Continued therapy with the pursuit of the "leak proteinuria" starting to emerge from day 23 on would have completely reversed the mild edema and mild hypertension that developed as an outpatient, needing the use of diuretics and co-channel blockers.

Complete clinical remission of uremic renal failure, anti-phospholipid antibody/acquired thrombopathy/lupus anti-coagulant with complete laboratory remissions of renal, immunological and hematological parameters were accomplished. No remission (inadequate duration of therapy) of anemia or proteinuria were observed.

Like Patient No. 7, this patient showed the disappearance of an immunological parameter (ANA-patient No. 5 completely), parallel to the lupus anti-coagulant with the healing of the renal lesion. Patient No. 8 with a total therapeutic dose of 5,150 mg/kg given over 27 days showed a remarkably swift and complete renal/hematological recovery (in conventional medicine terms), in contrast to patient No. 14 with the same disease entity who received a total therapeutic dose of 14,560 mg/kg over 285 days with only partial renal recovery.

Patient No. 9

Initial Pathological State

Thrombotic microangiopathy—TNF/Mitomycin C-Acquired thrombopathy, breast cancer/Stage IV.

Result of Therapy

This patient had received TNF and Mitomycin-C therapy for breast cancer resilient to other medical therapy. As a result, a subacute poorly defined form of thrombotic microangiopathy picture developed with elevated parameters of endothelial cell injury markers of AgPAI1, endothelin-I, low levels of protein SI, marked thrombopathy with impaired platelet aggregation of arachidonic acid, ADP 5, and high levels of ongoing cytokine levels of sIL2R and TNF, as well as Natural Killer Cells. Treatment at dose levels of 40–80 mg/kg/day, which levels were inductive of complete cure in patient No. 5 with a very acute lesion, failed to treat the subacute chronic lesion of Patient No. 9. It can be seen that following only disease markers, is a less than satisfactory way to adjust dose, especially in chronic established lesions, rather than following both disease and repair markers. Assessment of the impaired repair pathways of protein kinase A/C systems together with respective genomic levels of disease markers (as respective mRNA) are essential in determining proper dose.

Patient No. 10

Initial Pathological State

Idiopathic hemolytic uremic syndrome auric renal failure, nephrogenic hypertension, microangiopathic hemolysis consumptive thrombocytopenia.

Result of Therapy

This patient represents an example for marker-non-dependent dose assessment.

Patient No. 10 showed an initial decline of fPAI, with increasing platelet counts on 60 mg/kg/day dose, yet subsequent increase in fPAI in spite of continuing hematological recovery.

Patient No. 10 represents failure to increase the dose to push vWAg levels higher. vWAg levels declined by day 20 in spite of an increase in dose from 60 to 80 mg/kg/day from day 8 to day 20. Increasing AgPAI1 disease marker levels should have been pursued to increase the dose high as necessary to increase the vWAg universal marker level to nearly 500% (5×) and disease marker AgPAI1 to completely normal levels. The decline on therapy of vWAg does not signify in this case completion of the repair event. Since no plateau in 5× elevated levels precedes decline on therapy, the vWAg decline in spite of modest increases in dose signify shifting of the lesion into a subacute/chronic phase. Utilization of protein kinase A/C pathway repair markers would have been invaluable to control and reverse this progression of pathology. This patient clearly indicates that recovery of hematological parameters do not negate worsening or ongoing pathology with the renal/vascular endothelial cells.

Patient No. 11

Initial Pathological State

Breast cancer/Stage IV prothrombotic state, bilateral femoral thrombi, bilateral lower extremity deep vein thrombosis, bilateral ischemic soft tissue necrosis of toes, acquired thrombopathy.

Result of Therapy

Patient No. 11 represents successful thrombolytic/doses corresponding very clearly to increasing AgTPA levels and decreasing AgPAI1 levels for the duration of therapy with the clinical events of dissolution of bilateral hemoral thrombi. Cessation of therapy led to recurrent pathology of declining AgTPA and increasing fPAI and AgPAI1 levels. This represents failure to follow the markers adequately to ensure complete thrombolytic therapy.

Patient No. 11 represent adequate doses for irreversible control of the prothrombotic state, since antithrombotic molecules remain at normal levels of therapy. This represents a clear example of how the pleiotropic action of the nucleotide is completely dependent on the stratified dose levels, different dose levels governing different actions of the nucleotide ranging from modulation of the redox state, for example to genomic modulation.

This patient showed resurgence of the endothelial cell lesion with the two representative disease markers of TNF and endothelin-I. Both markers had to be followed for complete cure of the concurrent soft-tissue necrosis involving bilateral toes, partial therapy, administered at that respective stage of the development of marker dependent dose-assessment, led in this patient to complete disappearance of the inflammatory findings involving both lower extremities, demarcation of the necrotic toe lesions but not complete disappearance thereof. This was in contrast to patient No. 7, where the necrotic lesions were healed completely.

While dose levels given to both patient Nos. 8 and 4 were about 80 mg/kg/day (maximum efficacious dose), the total therapeutic dose was significantly higher in patient No. 7 with complete cure (198 mg/kg) compared to patient No. 11 with partial response (818 mg/kg).

Patient No. 12

Initial Pathological State

Thrombotic microangiopathy, consumptive thrombocytopenia, microangiopathic hemolysis, Stage IV breast cancer, pro-thrombotic state, auric renal failure, nephrogenic hypertension.

Result of Therapy

This patient was treated with conventional doses of <40 mg/kg/day for the treatment of renal disease. Inadequate response at <40 mg/kg/day dose in antithrombotic molecules are represented by patient No. 12. While successful hematological recovery with <40 mg/kg/day is shown in patient No. 12, inadequate elevation of vWAg, inadequate elevation of AgTPA, and inadequate therapeutic effect at <40 mg/kg/day dose was shown for renal disease (creatine endothelin-I (nephrogenic hypertension)). Inadequate suppressions of TNF and sIL2R were also observed at a dose of <40 mg/kg/day;

Patient No. 13

Initial Pathological State

Congenital hepatic vein thrombosis (Banti's Syndrome) prothrombotic state with recurrent deep vein thrombosis of left axillary vein and left subclavian vein, thrombosis of sagittal and saphenous sinus, portal hypertension with gastric varices, recurrent GI bleeding, acquired thrombopathy, ascending cholangitis, ischemic parenchymal disease, dysfibrinogenemia.

Result of Therapy

This patent illustrates the biological interdependency of protein kinase C/A pathways, cell surface receptor/ligand interactions, and genomic transcriptional/translational activity. The administered nucleotide functioned to down regulate the protein kinase C/A pathways and genomic transcriptional/translational activity at the peak of the primary response, regardless of whether the response is hormonal secretion, immunological, autonomic nervous, prothrombotic, and/or transcriptional.

Complete clinical remissions for ascending cholangitis, deep vein thrombosis, inflammatory signs and cessation of gastrointestinal bleeding was observed. Remission of the prothrombotic state coincided with titration of dose, i.e., different dose levels with different disease state based on various laboratory markers of protein CA, protein CI and protein SI. Concurrent with cessation of bleeding from the GI tract, the thrombi involving the cranial sinuses were relieved which demonstrated that the drug, irrespective of dose, will induce only enough of the concurrent (yet seeming opposing) molecular event (e.g., antithrombotic, anti-inflammatory, fibrindytic and hemostatic actions) as directed at the transcriptional/translational level by the cells, i.e., under-regulation at the genomic level.

Clinically, left upper extremity edema/pain disappeared without resolution of the thrombotic proximal vascular occlusion involving the left auxiliary vein confirming that the nucleotide effectively treats deep vein thrombosis, i.e., tissue healing without necessarily dissolving the thrombosis.

Patent No. 13 showed, impaired arachidonic acid aggregation with elevated liver functions, high WBC count (IL-6 induced response) and amelioration thereof with nucleotide therapy. Normalization of arachidonic acid aggregation occurred with increasing DKGD. The inhibiting action of the nucleotide upon the protein kinase C pathway was represented by decreased endothelin-I levels and the dose dependency thereof. Nucleotide therapy was found to induce a decline in AgPAI1 level without concurrent elevation in AgTPA but which is concurrent with protein CA level.

Patient No. 14

Initial Pathological State

Idiopathic hemolytic uremic syndrome, nephrogenic hypertension, lupus anti-coagulant consumptive thrombopathy, microangiopathic hemolysis.

Result of Therapy

This patient shows that treatment of a subsequently identified second marker leads to the further amelioration of the first marker. Partial/near complete regaining of renal function was accompanied by the nucleotide induced treatment of nephrogenic hypertension. Dose dependent reproducible variation in vWAg levels confirms that automatic elevation of thrombolytic molecule AgTPA will not take place only by virtue of the on therapy declining AgPAIl levels, if elevation of AgTPA transcriptional activity is not specifically needed for the treatment of the particular lesion.

AgPAI1 elevation in this patient reflected endothelial cell injury, as proven by the fact that its successful treatment also corrected endothelin-I levels. The effect on the endothelin-I levels were dose dependent and recurred off therapy, necessitating antihypertensives. If this patient's maximum therapeutic dose level had been adjusted so as to discontinue therapy only when vWAg levels on therapy declined to normal, nephrogenic hypertension and renal function would be irreversible corrected.

What is claimed is:

1. A method of treating a disease condition in a patient selected from the group consisting of vascular disease, veno-occlusive disease, thrombotic microangiopathy, acquired thrombopathy, glomular proteinuria, renal failure, nephrogenic hypertension, hemolytic uremic syndrome, primary anti-phospholipid antibody syndrome, prothrombotic state secondary to anti-phospholipid antibody, anti-phospholipid antibody dependent acute myocardial infarction, acquired platelet abnormality, adult respiratory distress syndrome, subendocardial myocardial infarction, soft tissue necrosis, arthralgia, tuberculosis, and herpes, comprising the following steps:

(a) determining the initial state of a set of disease markers associated with the disease condition, the disease markers being observable characteristics of a patient which deviate from a normal condition due to the disease state and wherein each disease marker in the set has a predetermined reference range which is indicative of the normal condition, (b) administering to the patient a dose of a therapeutic compound wherein the amount is between 40 mg/kg patient body weight per day to 250 mg/kg patient body weight per day comprising defibrotide, (c) screening a panel of second messengers and signal transducers and selecting a repair marker, the intensity of which increases following administration of defibrotide, where intensity is the extent to which the state of the repair marker differs from its state in the normal condition, said repair marker being the concentration of a compound which participates in a cellular regulatory pathway which operates through protein kinase A, protein kinase C, or G-protein, (d) administering defibrotide at a dose level incrementally higher than the previous dose, (e) repeating step (d) each time the intensity of the repair marker increases, (f) repeating steps (d) and (e) until the intensity of the repair marker in step (c) no longer increases, (g) continuing administration of defibrotide at the highest dose level attained in step (f) until the intensity of the repair marker returns to the normal condition, and (h) administering defibrotide at a dose level incrementally higher than the previous dose and repeating steps (c), (d), (e),(f) and (g) with one or more additional repair markers until all disease markers of said set of disease markers no longer deviate from the normal condition.

2. The method of claim 1 further comprising:

(i) monitoring repair markers selected in steps (c) and (h) for 3 weeks following the last dose of the therapeutic compound given in step (h) and if the intensity of one or more repair markers deviate from the normal condition, reinitiating therapy in step (g) at the highest dose level achieved in step (h).

3. The method of claim 1 wherein said disease is a viral disease and the disease marker is the concentration of a compound selected from the group consisting of viral proteins, viral RNA and viral DNA.

4. The method of claim 1 wherein defibrotide is administered intravenously, orally or topically.

5. The method of claim 1 wherein the dose of defibrotide is from about 40 mg/kg patient body weight per day to about 350 mg/kg patient body weight per day and defibrotide is high molecular weight defibrotide.

6. The method of claim 1 wherein the dose of defibrotide is from about 40 mg/kg patient body weight per day to about 600 mg/kg patient body weight per day and defibrotide is low molecular weight defibrotide.

7. A method of treating a disease condition in a patient selected from the group consisting of vascular disease, veno-occlusive disease, thrombotic microangiopathy, acquired thrombopathy, glomular proteinuria, renal failure, nephrogenic hypertension, hemolytic uremic syndrome, primary anti-phospholipid antibody syndrome, prothrombotic state secondary to anti-phospholipid antibody, anti-phospholipid antibody dependent acute myocardial infarction, acquired platelet abnormality, adult respiratory distress syndrome, subendocardial myocardial infarction, soft tissue necrosis, arthralgia, tuberculosis, and herpes, comprising the following steps:

(a) determining the initial state of a set of disease markers associated with the disease condition, the disease markers being observable characteristics of a patient which deviate from a normal condition due to the disease state and wherein each disease marker in the set has a predetermined reference range which is indicative of the normal condition, (b) administering to the patient a dose of a therapeutic compound wherein the amount is between 40 mg/kg patient body weight per day to 250 mg/kg patient body weight per day comprising defibrotide, (c) screening a panel of second messengers and signal transducers and selecting a repair marker, the intensity of which increases following administration of defibrotide, where intensity is the extent to which the state of the repair marker differs from its state in the normal condition, the repair marker being the concentration of a compound which participates in a cellular regulatory pathway which operates through protein kinase A, protein kinase C, or G-protein, (d) administering defibrotide at a dose level incrementally higher than the previous dose, (e) repeating step (d) each time the intensity of the repair marker increases, (f) repeating steps (d) and (e) until the intensity of the repair marker in step (c) no longer increases, (g) administering defibrotide at the dose level where the intensity of the repair marker no longer increases until the intensity of the repair marker returns to the normal condition, (h) administering defibrotide at a dose level incrementally higher than the previous dose and repeating steps (c), (d), (e), (f) and (g) with one or more additional repair markers until all disease markers of said set of disease markers no longer deviate from the normal condition, and (i) administering defibrotide at a dose level incrementally higher than the previous dose given in step (h) and repeating steps (c), (d), (e), (f) and (g) until the intensity of a universal marker, vWAg, returns to the concentration found in an uninfected individual.

8. a) (1) The method of claim 10 further comprising:

(j) monitoring the universal marker for 3 weeks following the last dose given in step (i) and if the intensity deviates from the normal condition, reinitiating therapy at step (i) at the highest dose level achieved in step (i).

9. A method of treating a disease condition in a patient selected from the group consisting of vascular disease, veno-occlusive disease, thrombotic microangiopathy, acquired thrombopathy, glomular proteinuria, renal failure, nephrogenic hypertension, hemolytic uremic syndrome, primary anti-phospholipid antibody syndrome, prothrombotic state secondary to anti-phospholipid antibody, anti-phospholipid antibody dependent acute myocardial infarction, acquired platelet abnormality, adult respiratory distress syndrome, subendocardial myocardial infarction, soft tissue necrosis, arthralgia, tuberculosis, and herpes, comprising the following steps:

(a) determining the initial state of a set of disease markers associated with the disease condition, the disease markers being observable characteristics of a patient which deviate from a normal condition due to the disease state and wherein each disease marker in the set has a predetermined reference range which is indicative of the normal condition, (b) administering to the patient a dose of a therapeutic compound comprising defibrotide, wherein the dose of defibrotide is at a level which raises a universal marker to at least five times its normal level, the universal marker being, von Willebrandt antigen (vWAg), a constitutively expressed molecule which is transcriptionally activated by the therapeutic compound in all disease states, and (c) continuing to administer defibrotide at the dose level of step (b) until the universal marker returns to its normal level.

10. The method of claim 9 further comprising:

(d) monitoring the universal marker for 3 weeks following the last dose given in step (c) and if the intensity deviates from the normal condition, reinitiating therapy at step (c).

11. The method of claims 1, 5 or 6 wherein the administration of defibrotide induces fibrinolysis.

12. The method of claim 11 wherein the dose of defibrotide in step (b) is from about 240 mg/kg patient body weight per day to about 300 mg/kg patient body weight per day.

13. The method of claims 1, 5 or 6 wherein the administration of defibrotide induces activation of protein kinase A or protein kinase C.

14. The method of claim 13 wherein the dose of defibrotide in step (b) is from about 240 mg/kg patient body weight per day to about 300 mg/kg patient body weight per day.

15. The method of claims 1, 5 or 6 wherein the administration of defibrotide induces antithrombotic action.

16. The method of claim 15 wherein the dose of defibrotide in step (b) is from about 80 mg/kg patient body weight per day to about 200 mg/kg patient body weight per day.

17. The method of claims 1, 5 or 6 wherein the administration of defibrotide induces proplatelet action.

18. The method of claim 17 wherein the dose of defibrotide in step (b) is from about 120 mg/kg patient body weight per day to about 200 mg/kg patient body weight per day.

19. The method of claims 1, 5 or 6 wherein the disease condition is a prothrombotic state secondary to anti-phospholipid antibody or primary anti-phospholpid antibody disease and wherein the dose of defibrotide in step (b) is from about 60 mg/kg patient body weight per day to about 200 mg/kg patient body weight per day.

20. The method of claims 1, 5 or 6 wherein the disease condition is renal failure, nephrogenic hypertension, thrombotic microangiopathy, or hemolytic uremic syndrome and wherein the dose of defibrotide in step (b) is at least 60 mg/kg patient body weight per day.

21. The method of claim 20 wherein the dose of defibrotide in step (b) is from about 150 mg/kg patient body weight per day to about 250 mg/kg patient body weight per day.

22. The method of claims 1, 5, 6 wherein the disease condition is anti-phospholipid antibody dependent acute myocardial infarction or adult respiratory distress syndrome and wherein the dose of defibrotide in step (b) is from about 60 mg/kg patient body weight per day to about 200 mg/kg patient body weight per day.

23. The method of claims 1, 5 or 6 wherein the disease condition is acquired thrombopathy and wherein the dose of defibrotide in step (b) is from about 120 mg/kg patient body weight per day to about 250 mg/kg patient body weight per day.

24. The method of claim 1, 5 or 6 wherein the administration of defibrotide induces activation or repression of genomic transcription.

25. The method of claim 24 wherein the dose of defibrotide in step (b) is from about 40 mg/kg patient body weight per day to about 400 mg/kg patient body weight per day.

* * * * *